(12) United States Patent
Bianchi et al.

(10) Patent No.: US 11,083,642 B2
(45) Date of Patent: *Aug. 10, 2021

(54) ABSORBENT ARTICLES WITH COLORED TOPSHEET

(71) Applicant: The Procter & Gamble Company, Cincinnati, OH (US)

(72) Inventors: Ernesto Gabriel Bianchi, Oberursel (DE); Theodore Cory Fites, Cincinnati, OH (US); Nicole Anja Reichardt, Sulzbach (DE); Thomas Walenzyk, Kriftel (DE)

(73) Assignee: The Procter & Gamble Company, Cincinnati, OH (US)

( * ) Notice: Subject to any disclaimer, the term of this patent is extended or adjusted under 35 U.S.C. 154(b) by 420 days.

This patent is subject to a terminal disclaimer.

(21) Appl. No.: 15/921,692

(22) Filed: Mar. 15, 2018

(65) Prior Publication Data
US 2018/0200124 A1    Jul. 19, 2018

Related U.S. Application Data

(63) Continuation of application No. 15/361,573, filed on Nov. 28, 2016, now Pat. No. 10,864,119.
(Continued)

(51) Int. Cl.
*A61F 13/513* (2006.01)
*A61F 13/49* (2006.01)
(Continued)

(52) U.S. Cl.
CPC ........ *A61F 13/51394* (2013.01); *A61F 13/49* (2013.01); *B65D 85/62* (2013.01);
(Continued)

(58) Field of Classification Search
CPC ............... A61F 13/49; A61F 13/51394; A61F 2013/51002; A61F 2013/51014; A61F 13/42; A61F 13/514
See application file for complete search history.

(56) References Cited

U.S. PATENT DOCUMENTS 3,848,594 A    11/1974  Buell
3,860,003 A     1/1975  Buell
(Continued)

FOREIGN PATENT DOCUMENTS

| CN | 104822352 A | 8/2015 |
|---|---|---|
| CN | 104837458 A | 8/2015 |
| EP | 149880 | 7/1985 |
| EP | 2399558 | 12/2011 |
| WO | WO95/11652 | 5/1995 |
| WO | WO95/34329 | 12/1995 |
| WO | WO2000/71067 | 11/2000 |
| WO | WO2003/053313 | 7/2003 |
| WO | WO2005/105010 | 11/2005 |
| WO | WO2008/155699 | 12/2008 |

(Continued)

OTHER PUBLICATIONS

All Office Actions, U.S. Appl. No. 15/361,573.
International Search Report, PCT/US2016/060045, dated Jan. 27, 2017, 13 pages.

*Primary Examiner* — Michele M Kidwell
(74) *Attorney, Agent, or Firm* — Wednesday G. Shipp

(57) ABSTRACT

An absorbent article has a wearer-facing side and a garment-facing side. The article also has a topsheet on the wearer-facing side; a backsheet; an absorbent core disposed between the topsheet and the backsheet; an acquisition layer disposed between the absorbent core and the topsheet; and a visual signal viewable from the wearer-facing side of the absorbent article. The visual signal includes a color imparted to the acquisition layer. The article further comprises at least one channel disposed within the absorbent core that is substantially free of absorbent material; and a wetness indicator disposed on the backsheet and viewable from the garment-facing side of the absorbent article.

13 Claims, 7 Drawing Sheets

Related U.S. Application Data

(60) Provisional application No. 62/260,745, filed on Nov. 30, 2015.

(51) Int. Cl.
*A61F 13/51* (2006.01)
*B65D 85/62* (2006.01)

(52) U.S. Cl.
CPC .............. *A61F 2013/51002* (2013.01); *A61F 2013/51014* (2013.01)

(56) References Cited

U.S. PATENT DOCUMENTS

| | | | |
|---|---|---|---|
| 4,515,595 A | 5/1985 | Kievet et al. | |
| 4,623,340 A * | 11/1986 | Luceri | A61F 13/15577 |
| | | | 604/385.05 |
| 4,662,875 A | 5/1987 | Hirotsu et al. | |
| 4,695,278 A | 9/1987 | Lawson | |
| 4,710,189 A | 12/1987 | Lash | |
| 4,795,454 A | 1/1989 | Dragoo | |
| 4,808,178 A | 2/1989 | Aziz et al. | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 5,137,537 A | 8/1992 | Herron et al. | |
| 5,151,092 A | 9/1992 | Buell et al. | |
| 5,221,274 A | 6/1993 | Buell et al. | |
| 5,439,458 A * | 8/1995 | Noel | A61F 13/15203 |
| | | | 604/378 |
| 5,486,166 A * | 1/1996 | Bishop | A61F 13/15203 |
| | | | 604/366 |
| 5,549,791 A | 8/1996 | Herron et al. | |
| 5,858,515 A | 1/1999 | Stockes et al. | |
| 6,075,178 A * | 6/2000 | La Wilhelm | A61F 13/42 |
| | | | 604/358 |
| 6,075,179 A | 6/2000 | McCormack et al. | |
| 6,307,119 B1 * | 10/2001 | Cammarota | A61F 13/42 |
| | | | 604/361 |
| 6,336,922 B1 | 1/2002 | VanGompel et al. | |
| 6,432,098 B1 | 8/2002 | Kline et al. | |
| 6,645,569 B2 | 11/2003 | Cramer et al. | |
| 6,790,798 B1 | 9/2004 | Suzuki | |
| 6,863,933 B2 | 3/2005 | Cramer et al. | |
| 7,112,621 B2 | 9/2006 | Rohrbaugh et al. | |
| 7,241,280 B2 * | 7/2007 | Christon | A61F 13/472 |
| | | | 604/385.01 |
| 7,744,576 B2 | 6/2010 | Busam et al. | |
| 7,786,341 B2 | 8/2010 | Schneider et al. | |
| 8,186,296 B2 | 5/2012 | Brown et al. | |
| 8,585,666 B2 | 11/2013 | Weisman et al. | |
| 10,864,119 B2 * | 12/2020 | Bianchi | A61F 13/51394 |
| 2003/0014025 A1 * | 1/2003 | Allen | A61F 13/42 |
| | | | 604/361 |
| 2003/0105190 A1 | 6/2003 | Diehl et al. | |
| 2003/0148684 A1 | 8/2003 | Cramer et al. | |
| 2005/0008839 A1 | 1/2005 | Cramer et al. | |
| 2006/0004333 A1 * | 1/2006 | Olson | A61F 13/42 |
| | | | 604/361 |
| 2006/0025737 A1 * | 2/2006 | Song | A61F 13/15203 |
| | | | 604/385.01 |
| 2006/0070701 A1 | 4/2006 | Kobayashi | |
| 2006/0111684 A1 * | 5/2006 | Berba | A61F 13/51496 |
| | | | 604/361 |
| 2006/0149198 A1 * | 7/2006 | Liu | A61F 13/42 |
| | | | 604/361 |
| 2006/0161122 A1 * | 7/2006 | Erdman | A61F 13/53747 |
| | | | 604/378 |
| 2007/0118087 A1 | 5/2007 | Flohr | |
| 2008/0071239 A1 * | 3/2008 | Nandrea | A61F 13/42 |
| | | | 604/361 |
| 2008/0206529 A1 | 8/2008 | Ueminami | |
| 2008/0312622 A1 * | 12/2008 | Hundorf | A61F 13/5323 |
| | | | 604/366 |
| 2009/0157021 A1 * | 6/2009 | Sullivan | A61F 13/51496 |
| | | | 604/359 |
| 2009/0281513 A1 * | 11/2009 | Nelson | A61F 13/511 |
| | | | 604/379 |
| 2010/0036346 A1 * | 2/2010 | Hammons | A61F 13/51305 |
| | | | 604/378 |
| 2010/0168695 A1 * | 7/2010 | Robles | A61F 13/42 |
| | | | 604/361 |
| 2010/0168700 A1 * | 7/2010 | Schmidt | A61F 13/42 |
| | | | 604/361 |
| 2010/0286644 A1 * | 11/2010 | Li | A61F 13/15 |
| | | | 604/385.01 |
| 2010/0310837 A1 | 12/2010 | Bond | |
| 2011/0028929 A1 * | 2/2011 | Hopkins | A61F 13/84 |
| | | | 604/383 |
| 2011/0073513 A1 | 3/2011 | Weisman et al. | |
| 2011/0137624 A1 | 6/2011 | Weisman et al. | |
| 2011/0250413 A1 | 10/2011 | Lu et al. | |
| 2011/0268932 A1 | 11/2011 | Catalan et al. | |
| 2011/0274834 A1 | 11/2011 | Brown | |
| 2011/0319848 A1 | 12/2011 | McKiernan et al. | |
| 2012/0010581 A1 * | 1/2012 | Mason, Jr. | A61F 13/5514 |
| | | | 604/359 |
| 2012/0165776 A1 * | 6/2012 | McGregor | A61L 15/22 |
| | | | 604/372 |
| 2012/0308787 A1 * | 12/2012 | Kozee | B41J 3/407 |
| | | | 428/195.1 |
| 2012/0316532 A1 | 12/2012 | Mccormick | |
| 2013/0158492 A1 * | 6/2013 | Song | A61L 15/56 |
| | | | 604/361 |
| 2014/0044934 A1 * | 2/2014 | Bills | A61F 13/51496 |
| | | | 428/196 |
| 2014/0114271 A1 * | 4/2014 | Arora | A61F 13/15203 |
| | | | 604/385.01 |
| 2014/0148773 A1 * | 5/2014 | Brown | A61F 13/4902 |
| | | | 604/361 |
| 2014/0163506 A1 * | 6/2014 | Roe | A61F 13/49007 |
| | | | 604/378 |
| 2014/0228795 A1 | 8/2014 | Castanares | |
| 2014/0296815 A1 * | 10/2014 | Takken | A61F 13/512 |
| | | | 604/383 |
| 2015/0080837 A1 | 3/2015 | Rosati et al. | |
| 2015/0080839 A1 | 3/2015 | Trapp et al. | |
| 2015/0173968 A1 * | 6/2015 | Joseph | A61F 13/532 |
| | | | 604/361 |
| 2016/0074247 A1 * | 3/2016 | Rosati | A61F 13/551 |
| | | | 604/378 |
| 2017/0151103 A1 | 6/2017 | Bianchi et al. | |

FOREIGN PATENT DOCUMENTS

| | | |
|---|---|---|
| WO | WO2011015956 A2 | 2/2011 |
| WO | WO2011041352 A1 | 4/2011 |
| WO | WO2011/163046 | 12/2011 |
| WO | WO2012/052172 | 4/2012 |
| WO | W02012154444 A1 | 11/2012 |
| WO | WO2012/170341 | 12/2012 |
| WO | WO2012/170778 | 12/2012 |
| WO | WO2012/170779 | 12/2012 |
| WO | WO2012/170781 | 12/2012 |
| WO | WO2012/170808 | 12/2012 |
| WO | WO2012/177400 | 12/2012 |
| WO | WO2012/177401 | 12/2012 |
| WO | WO2014/078247 | 5/2014 |
| WO | WO2014/093323 | 6/2014 |
| WO | WO2014/200794 | 12/2014 |
| WO | WO2015/039062 | 3/2015 |

* cited by examiner

ABSORBENT ARTICLES WITH COLORED TOPSHEET

FIELD OF THE INVENTION

The invention relates to absorbent articles such as taped diapers or diaper pants. The articles of the invention have an improved appearance on their wearer-facing side obtained in a simple and cost effective manner.

BACKGROUND OF THE INVENTION

Absorbent articles for personal hygiene of the type indicated above are designed to absorb and contain body exudates, in particular large quantity of urine. These absorbent articles comprise several layers, typically a topsheet on the wearer-facing side, a backsheet on the garment-facing side and in-between an absorbent core, among other layers. An acquisition and/or a distribution layer may be further provided between the absorbent core and the topsheet. Many diapers comprise on their backsheet a printed ornamentation comprising geometric shapes and/or cartoon like characters.

Absorbent articles with a colored ornamentation on the topsheet, i.e. the wearer-facing side are much less common. WO2003/053313A1 (Christen et al.) discloses feminine hygiene products having a signal viewable from the top surface of the absorbent article which gives a perception of depth within the absorbent article. The depth perception is accomplished by a printed signal comprising two shades operating together to create a perception of depth within the absorbent article. The example shows a darker shade positioned centrally in relation to a lighter shade surrounding it.

More recently, WO2014/078247 (Rosati et al.) discloses absorbent articles having a topsheet, a backsheet, an absorbent core, and a printed adhesive layer disposed between the topsheet and the absorbent core. The absorbent core may comprise channels, and the adhesive print layer may be visible through the topsheet. WO2015/039062 (Tapp et al.) further discloses that the printed adhesive layer forms a pattern of one or more pairs of contoured lines that run lengthwise in the machine direction of the absorbent article, each pair being symmetric to its compliment across an axis of the absorbent article drawn in the machine direction and at the center of its width. The distance between the innermost pair of contoured lines is from 15 mm to 25 mm. The pattern coverage with the adhesive may be from about 15% to about 30%.

There is a continuous need to improve the visual appearance of absorbent articles in a simple and cost-efficient manner.

SUMMARY OF THE INVENTION

The present invention is for an absorbent article that comprises a topsheet on the wearer-facing side, a backsheet on the garment-facing side, and an absorbent core between the topsheet and the backsheet. The absorbent core may comprise absorbent material comprising fibers and superabsorbent polymer material. The article further comprises a visual signal visible on the wearer-facing side. The visual signal may comprise a color imparted to the acquisition layer.

In other aspects, the visual signal may be a color imparted to the topsheet or a layer beneath the topsheet.

Still further, the article may further include a channel disposed in the absorbent core that is substantially free of absorbent material. In other nonlimiting embodiments, the visual signal may overlay the channel.

The visual signal may be printed or otherwise provided on an intermediate layer between and including the topsheet and the absorbent core, in particular a nonwoven acquisition layer. It is not excluded that the visual signal is provided on another layer, for example the garment-facing side of the topsheet or the wearer-facing side of the absorbent core. The topsheet is sufficiently transparent so that the visual signal is visible through the topsheet.

The visual signal may comprise a pattern of repeating elements that are clearly visible and identifiable through the topsheet to increase the perception of depth. The visual signal may in particular comprise a network of interconnecting lines formed by the first (colored) portion or the second (non-colored) portion, in particular wherein the interconnecting lines are oriented diagonally relative to the longitudinal axis, in particular at an angle of ±25°-70° relative to the longitudinal axis, and wherein the areas of the visual signal between the interconnecting lines form repeating units orientated in rows parallel to the interconnecting lines. It was found that these rows of repeating units may be particularly identifiable when they comprise from 3 to 7 repeating units, in particular from 4 to 6 repeating units. The visual signal may be provided by any known means, in particular the signal may be a printed signal. The ink used may be an adhesive ink thus further providing a structural benefit of the article in addition to a visual signal.

It may be advantageous that the topsheet should have a relatively low basis weight to be economical, in particular but not limited to nonwovens having a basis weight ranging from 10 gsm to 20 gsm. The topsheet may also have a larger basis weight for example up to 30 gsm or 40 gsm to provide a more lofty feel. The fibers of the nonwoven are stabilized by a pattern of thermal bonds, in particular calender bonds. Thermal bonds are typically used to increase the integrity of a nonwoven by providing inter-fiber bonds. It was also found that the visibility of the visual signal can be improved when the topsheet comprises thermal bonds. The best results are believed to be obtained when the total area of the thermal bonds ranges from 15% to 30% of the surface of the topsheet. The cumulated surface area of the plurality of thermal bonds may be from 19% to 25% of the total surface area of the topsheet. The thermal bonds may be all the same or the thermal bonds may differ in shape and/or orientation. At least some of the thermal bonds may advantageously have for example in particular a surface area of from 1 mm$^2$ to 6 mm$^2$.

BRIEF DESCRIPTION OF THE DRAWINGS

FIG. 3a shows a close up of a portion of the signal of FIG. 3;

DETAILED DESCRIPTION OF THE INVENTION

Introduction

Figure 1:
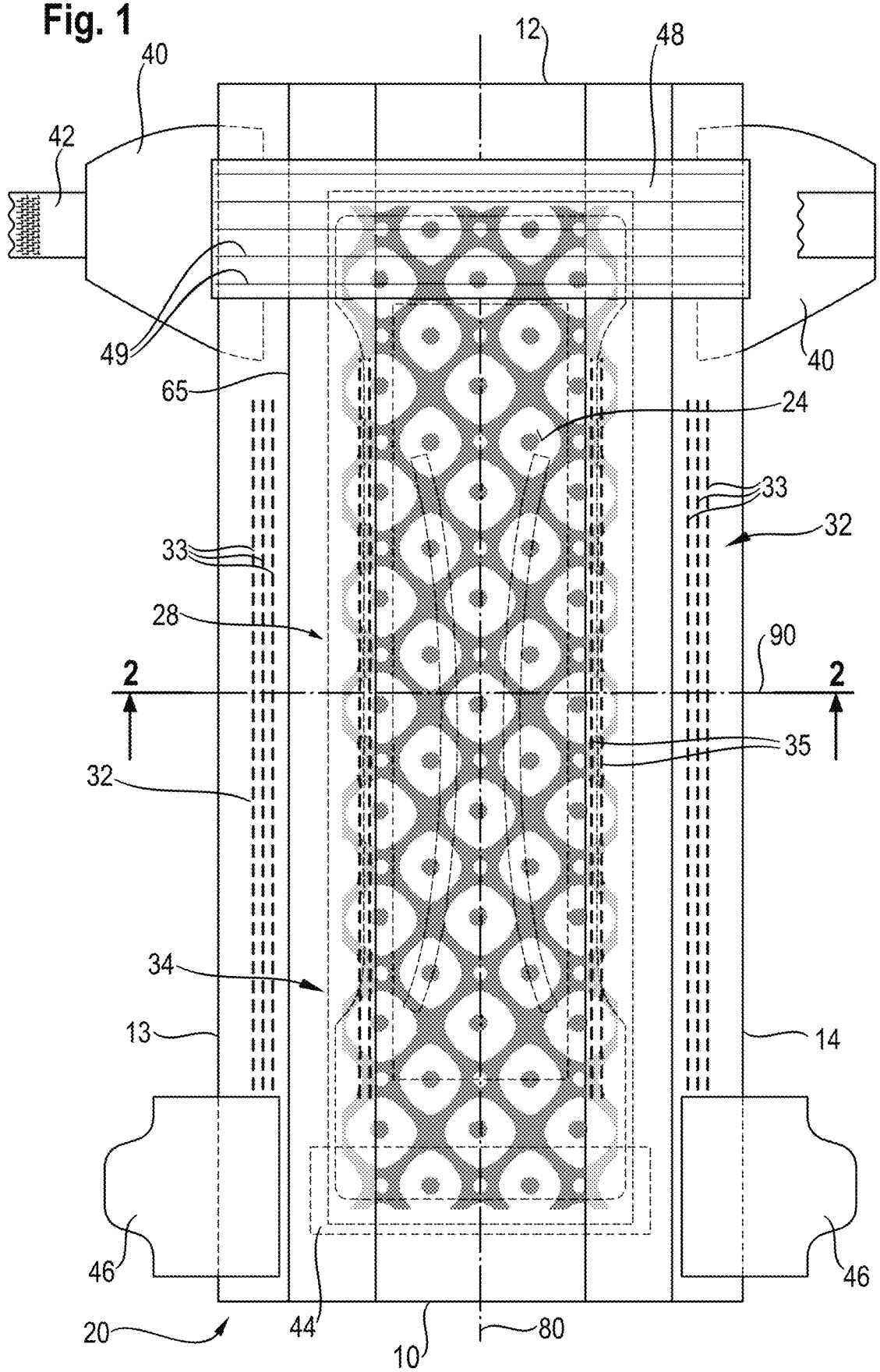
FIG. 1 is a top view of an exemplary absorbent article in the form of a taped diaper according to the invention.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

As used herein, the term "wearer" refers to an incontinent person, which may be an adult, a child, or a baby, and that will wear the absorbent article. The term "user" refers to the caregiver that applies the absorbent article on the wearer. The user may be a parent, a family member in general, a professionally employed caregiver or the wearer him/herself.

The term "nonwoven" is used herein in the usual sense in the art and means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to more than 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

The invention will now be further illustrated with reference to the embodiments as described in the Figures. For ease of discussion, absorbent articles and their components such as the absorbent core will be discussed with reference to the numerals referred to in these Figures. However it should be understood that these exemplary embodiments and the numerals are not intended to limit the scope of the claims, unless specifically indicated. Nothing in this description should be however considered limiting the scope of the claims unless explicitly indicated otherwise.

General Description of the Article 20

As used herein, the term "absorbent articles" refers to disposable products for personal hygiene which are placed against or in proximity to the body of the wearer to absorb and contain exudates discharged from the body, in particular urine. The absorbent articles will now be generally discussed and further illustrated in the form of a baby taped diaper 20 as exemplarily represented in FIG. 1. The diaper is illustrated in a flattened-out configuration with the back ears 40 and the front ears 46 unfolded and the wearer-facing side turned up. Such taped diapers are typically placed open on a flat surface as shown on FIG. 1, then the wearer such as a baby is placed on the open diaper, the front side of the diaper is then folded over the front waist of the wearer, and the back ears are then wrapped around the waist of the wearer and attached with the sticky parts 42 in a position adjacent the front waist of the diaper to close the diaper in place, typically on a so-called landing zone 44.

The invention is also applicable to other absorbent articles not further illustrated in the present application, in particular adult and infant diapers, including pants such as infant training pants and adult incontinence undergarments, and feminine hygiene products, such as sanitary napkins and panty-liners and adult incontinent pads. Pants have a pre-formed waist opening and leg openings and may be placed in position on the wearer by inserting the wearer's legs into the leg openings and sliding the pant up into position around the wearer's lower torso. A pant may be pre-formed by any suitable technique including, but not limited to, joining the front and back waist edges laterally using refastenable and/or non-refastenable bonds (e.g., seam, weld, adhesive, cohesive bond, fastener, etc.). A pant may be pre-formed anywhere along the circumference of the article (e.g., side fastened, front waist fastened).

The absorbent article typically has a front edge 10, a back edge 12 and two longitudinally-extending side edges 13, 14. The front edge 10 is placed in use towards the front of the wearer and the back edge 12 towards the back of the wearer. When the diaper is closed, the front and back edges form together with the ears 40, 46 the waist opening for the wearer. Each side edge 13, 14 forms one of the leg openings. The article has a longitudinal direction and a transverse direction defined by the longitudinal axis 80 and transversal axis 90 respectively. The longitudinal axis 80 extends through the middle of the front and back edges 10, 12 of the article, and thus virtually divides the article in symmetrical left side and right side. The article has a length L measured along the longitudinal axis 80 between the front and back edges of the article. The transversal axis 90 extends perpendicularly to the longitudinal axis and crosses the longitudinal axis at a position halfway between the front edge and the back edge (L/2 from the front and back edges). The transversal axis thus virtually defines a front half and a back half of the absorbent article. A pant-type diaper may also be placed flat in an open configuration as illustrated in FIG. 1 by opening its side seals.

Figure 2:
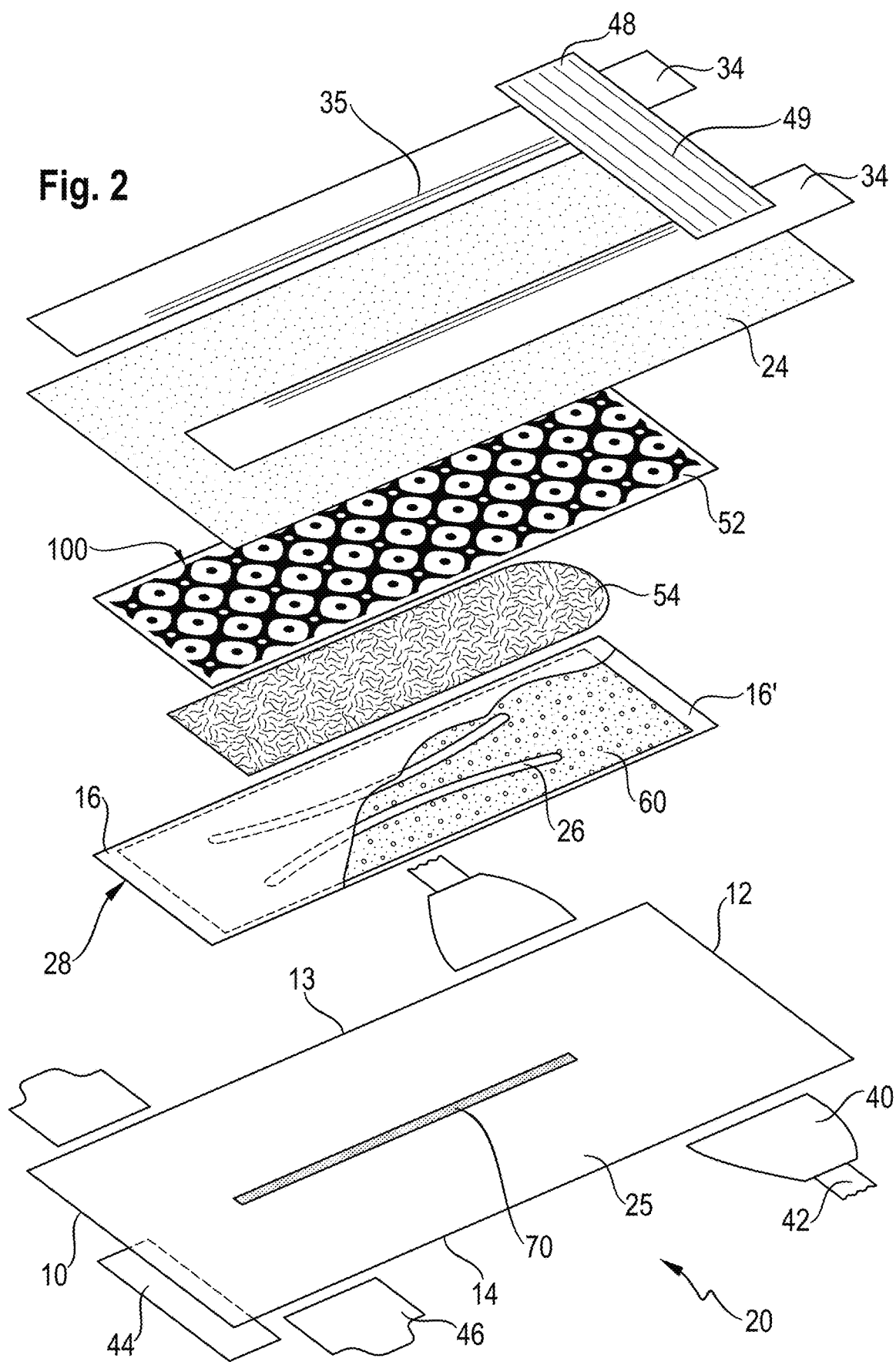
FIG. 2 is an exploded view of the diaper of FIG. 1.

FIG. 2 shows in an exploded view the components of the exemplary article individually. The wearer-facing side of the article comprises a fluid-permeable topsheet 24. The rest of the wearer-facing side of the diaper may comprise elasticized barrier leg cuffs 34 on the longitudinal sides of the diaper and optionally an elasticized back waist band 48. According to the present invention, the topsheet has a first color, for example provided by adding a pigment to the fibers forming the nonwoven topsheet. A backsheet 25 forms the opposite, garment-facing side of the diaper. Typically the backsheet comprises a liquid-impermeable film, which may be doubled externally by a softer non-woven layer. The backsheet film may comprise micro-pores to make the film vapor-permeable. Examples of topsheet and backsheet will be further discussed below. A wetness indicator 70, for example a hotmelt adhesive comprising a pH indicator, may be disposed as a stripe on another shape between the backsheet and the absorbent core as is known in the art.

The absorbent articles of the invention may further comprises an acquisition layer 52 (also called secondary-topsheet) placed underneath the topsheet. The acquisition layer may in particular be an air-through bonded carded nonwoven or a latex bonded spunbond layer, but any other type of acquisition layers can be used. The acquisition layer may typically be as wide (in transverse direction) and shorter (in longitudinal direction) as the absorbent core 28 underneath, but other dimensions are possible. The acquisition layer typically does not comprise SAP as this may slow the acquisition and distribution of the fluid. A distribution layer 54 be further optionally included between the topsheet and the absorbent core. A distribution layer may for example be a cross-linked cellulose layer, as is known in the art.

According to the invention, the absorbent article comprises a visual signal 100 visible from the wearer-facing side. "Visible" as used herein means capable of being perceived by the unaided human eye under usual light conditions. The visual signal may be present on the topsheet or a layer underneath the topsheet. For example the visual signal may be placed on the garment-facing side of the topsheet (also referred herein as the lower surface of the topsheet). Alternatively, and as represented in the FIGS. 2-3, the visual signal 100 may be disposed on the acquisition layer 52, in particular the visual signal may be disposed, e.g. by printing, on the upper or lower surface of the acquisition layer. As used herein "upper", or "top" refers to the surface or side of a layer which is orientated towards the wearer-facing side of the article, and "lower" or "bottom" refers to the surface or side of a layer orientated in the opposite direction, i.e. towards the garment-facing side. It is also possible that the visual signal may also be disposed on the upper surface of the top layer 16 of the core wrap, in particular if the article does not comprise an acquisition layer present between the topsheet and the absorbent core. Of course, the more layers are disposed between the visual signal and the wearer-facing side, the more difficult it will be for the user to perceive the visual signal through the topsheet.

Thus it may be advantageous that the visual signal is placed on layer directly underneath the topsheet such as on the acquisition layer, so that the visual signal does not have to go through another layer other than the topsheet before being visible on the wearer-facing side of the article. Acquisition layer are typically very thin and transparent so that it is not necessarily critical on which side the acquisition layer the visual signal is provided.

The visual signal according to the invention comprises a first portion 110 and a second portion 120. The first portion is typically obtained by treating the surface of one of the layers of the article to provide it with a different appearance than the second portion of the layer. In particular, the second portion may be an untreated portion of the layer on which the visual signal is present. In particular, the first portion may be a colored portion and the second portion a non-colored portion. The colored portion 110 may be obtained by printing the lower or the upper surface of the acquisition layer or the lower surface of the topsheet with a composition comprising an ink. In particular an adhesive composition comprising an ink may be used. It is however not excluded that the colored portion may be obtained by other means than printing, for example embossing, ring-rolling, or heat treatment may be sufficient to provide a first portion of the visible signal having a different appearance than the rest of the layer that has not been similarly treated. The second portion of the signal may correspond to the untreated portion of the layer on which the visual signal is applied, in particular the un-printed portion. The second portion can thus be defined negatively in relation to the first portion. The second portion may be in particular white if the layer on which the visual signal applied is white. As will be described in further details below, the visual signal may advantageously comprise a series of intersecting lines $210$-$21n$, $220$-$22n$ that form a grid pattern comprising rows of repeating units $250, 251, 252, 253$.

The absorbent article further comprises an absorbent core 28 between the topsheet 24 and the backsheet 25. The absorbent core may be according to any cores known in the art. Typically, absorbent cores comprise an absorbent material 60 which may be enclosed in a core wrap 16,16'. The absorbent material may typically comprise a mixture of cellulose fibers and superabsorbent polymer particles. The absorbent core may alternatively be free of cellulose fibers, as is known in so-called air-felt free cores. In air-felt free cores, the absorbent material comprises essentially superabsorbent polymers, which may be in the form of particles optionally immobilized by an adhesive within the core wrap. The superabsorbent polymers may be otherwise immobilized for example within pockets formed by ultrasonically bonding the top side and the bottom side of the core wrap along a grid. The core wrap may comprise a single substrate material completely wrapped around the absorbent material and forming the top side 16 and bottom side 16' of the core wrap. The core wrap may alternatively comprise two separate substrates respectively forming the bottom side and the top side of core wrap. One substrate may be wider than the other substrate to form flaps which are wrapped around the absorbent material and bonded to the other substrate in a C-wrap configuration. Core wrap substrates are typically nonwoven materials.

The absorbent core may optionally comprise a pair of generally longitudinally-extending areas 26 that are substantially free of absorbent material and through which the top side of the core wrap may be advantageously bonded to the bottom side of the core wrap. The area defined by absorbent material 60 within the core may be shaped with a recess on each of its longitudinal side or may be generally rectangular with straight longitudinally-extending side edges. Having briefly described different elements of the absorbent articles of the invention, these will now be further described and exemplified in more details in the following disclosure.

Visual Signal 100

Figure 3:
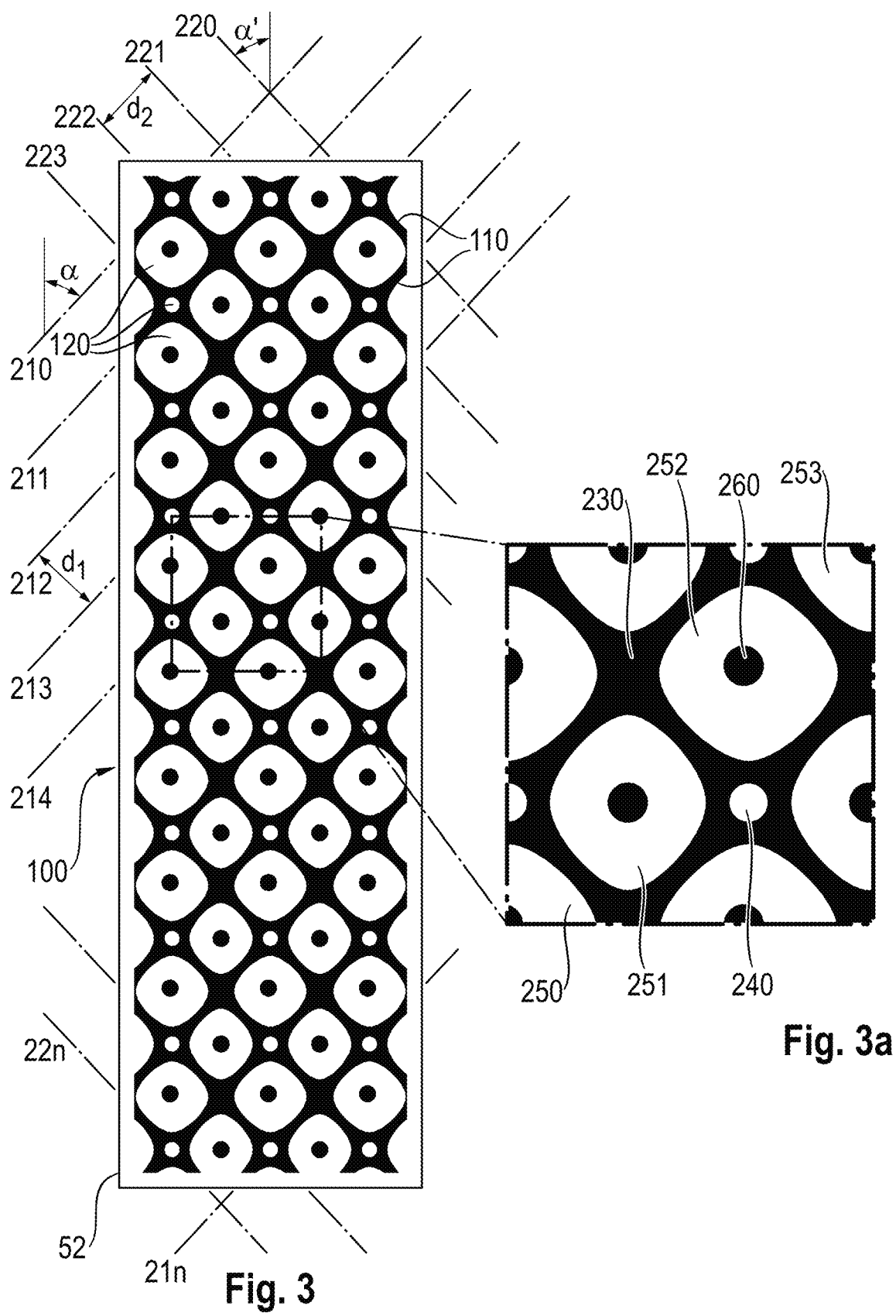
FIG. 3 shows an example of the visual signal according to the invention.
Figure 4:
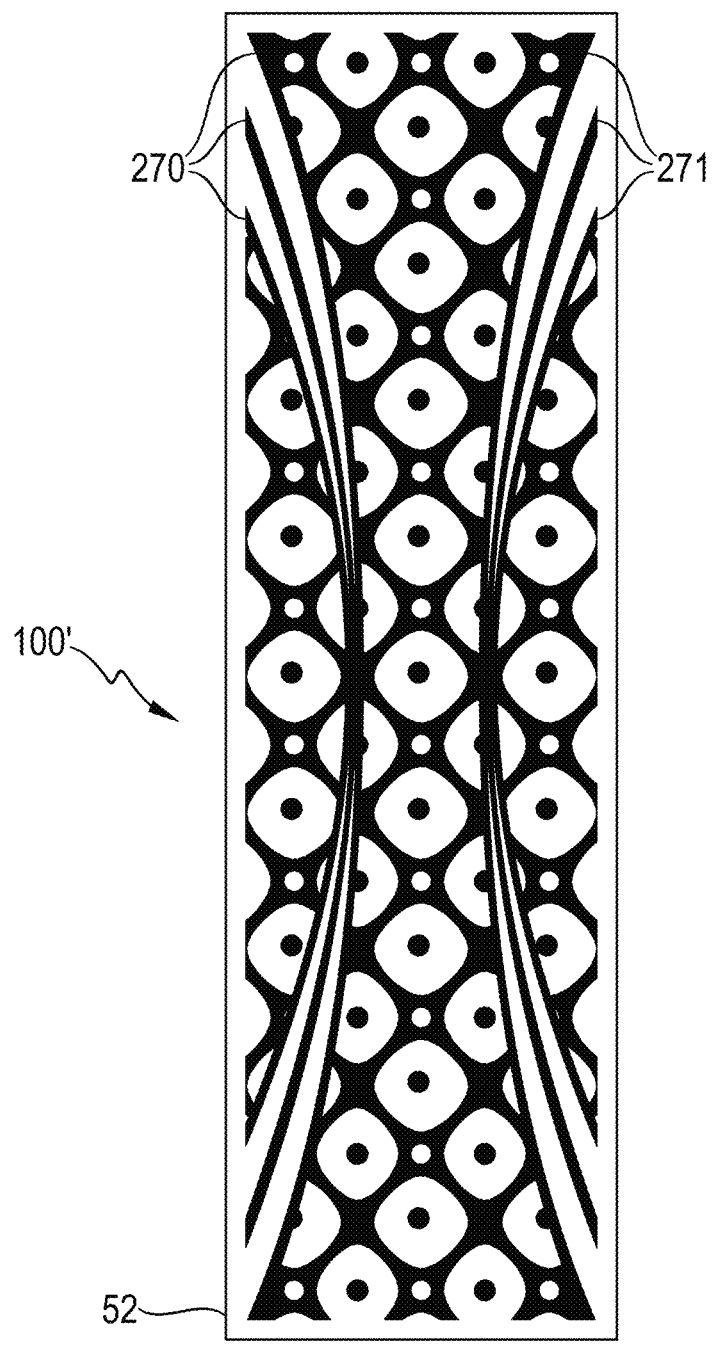
FIG. 4 shows another example of a visual signal.

FIGS. 3-4 illustrate two non-limiting examples of visual signals that may be used in the invention. The visual signal 100 may be applied to or otherwise provided on a layer of the article. The visual signal may be disposed for example on an acquisition layer 52 between the topsheet and the absorbent core, but it may also be disposed on the topsheet or the absorbent core, as indicated before. The visual signal comprises a first portion 110 having a first appearance and which corresponds to a portion of the layer that has been treated (in particular colored) to provide a contrasting appearance relative to a second portion 120 which is a non-treated (in particular non-colored portion) of the layer on which the visual signal is present. For example the first portion may be obtained by printing the layer with an ink having a certain color. The second portion is typically a non-colored portion of the layer which has not been treated to change its appearance. The visual signal may typically be applied on a layer having a generally white appearance, for example a film or a nonwoven layer which has does not comprise a colored pigment. Alternatively, it is not excluded that the visual signal may be applied on a layer which is colored, such as the topsheet. The first portion may in particular be obtained by printing a layer of the absorbent article with a colored ink, the second, non-colored portion being the rest of the layer which is not printed. Modern printing technologies can be used to create various printed patterns with accuracy and speed, such as those exemplarily illustrated in FIGS. 3-4. The term printing covers contact method such a print coating and non-contact method such as ink-jet or laser printing.

The ink used to print the visual signal may further comprise an adhesive so that the visual signal further serves to structurally attach the layers in-between which it was printed, such as the topsheet and the acquisition layer, or the acquisition layer and the core wrap, or the acquisition layer and a distribution layer if present. US2011/274834, U.S. Pat. No. 8,186,296 (Brown et al.) for example disclose apparatuses that can be used to apply viscous fluids, such as adhesives comprising a color change agent, in pre-determined patterns to an advancing substrate. The fluid application apparatus may include a slot die applicator and a substrate carrier. The substrate carrier may include one or more pattern elements and may be adapted to advance the substrate past the slot die applicator as the slot die applicator discharges adhesive onto the substrate. In operation, the substrate is disposed on the substrate carrier; the substrate carrier advances the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the substrate in an area having a shape substantially the same as a shape defined by the pattern surface. See also WO2014/078247 (Rosati et al.) for the application of this technology to create visual signal within an absorbent article.

The colored portion of the visual signal may be monocolor or comprise a plurality of different colors. It may be advantageous that the colored portion of the visual signal comprises a single color as this simplifies the making process of the article compared to the process of the prior art such as document WO2003/053313A1 where a dual color is printed. Rather, in the present invention, the dual color appearance on the wearer-facing side of the article is further achieved through the colored transparent topsheet, which is described in more details below.

The invention is not limited to a specific shape of the first portion of the visual signal. However it was found that certain visual signals could further provide an improved perception of depth to the user of the article. It was found that the visual signal may in particular comprise a network of intersecting lines to provide such an impression of depth. While not desiring to be bound by theory, it is believed that the lines may appear to the human brain as ditches where fluids may be more efficiently absorbed. This was reinforced if generally dot shaped inclusions 240, 260 are present in the visual signal, as will be discussed further, and also when at least some of the thermal bonds have an individual area of at least 1 mm$^2$. It was further found that the interconnecting lines are advantageously oriented diagonally relative to the longitudinal axis 80 of the article. "Diagonal" as used herein means an item disposed ±10°-80°, or ±25°-70°, or ±30°-60°, or ±45° with respect to longitudinal central axis of the article, disclosing for each range every 10° interval therebetween. This is for example illustrated by the printed colored lines 210, 211, . . . , 21n extending diagonally in one direction and intersecting with the printed colored lines 220, 221, . . . , 22n extending in another direction. The respective angles α and α' formed by these lines relative to the longitudinal centerline may be the same in absolute value. The distance d1 between two parallel lines orientated in the same direction may be the same for all line pairs. Likewise the distance d2 between two parallel lines orientated in the same direction may be the same for all line pairs. Advantageously, d1 and d2 may also have the same value.

As illustrated in the close-up view of FIG. 3a, the widths of the lines are not necessarily constant along their length. At the intersection of two lines, which may be described as a knot 230, the four corners of the cross formed by the intersecting lines may be rounded like a chamfer, as illustrated. Some or all of the knots 230 may further comprise an internal non-colored features or inclusions 240, which may be generally rounded as in a dot. The non-colored areas between the intersecting lines 210-21n, 220-22n define several rows of closed units 250, 251, . . . 25n. These rows are orientated in the same directions as the intersecting lines and extend from one longitudinal edge to the other edge of the visual signal. At least some of the rows may advantageously comprise from 3 to 7 closed units, in particular from 4 to 6 closed units. Units which are breaking at the edges of the visual signal and are therefore not completely closed are not counted for the purpose of assessing the numbers of units per rows. If too many units are present per row, the size of each unit diminishes in proportion and the resulting pattern may be difficult to recognize through the topsheet. The closed non-colored units 250-25n may be generally circular or ovoid, as exemplarily represented, but it not excluded that they may have other shapes, such as generally square, rectangular, parallelogrammatic, etc. One or more or all of these units may further comprise a colored inclusion 260 positioned towards its center. These colored inclusions 260 may be similar in size and shape to the non-colored inclusions 240 present at the knots 230 formed at the intersections of the colored lines. It was found that these inclusions, in particular the combination of colored and non-colored inclusions, further contribute to provide an impression of depth or absorbency to the user of the article.

FIG. 3 illustrates a first type of visual signal wherein the intersecting lines are part of the first, colored portion 110 and the units between the intersecting lines are part of the second, non-colored portion 120. It is also possible to have a visual signal where this is inverted i.e. where the intersecting lines are non-colored and the units between the lines are colored. Thus it is possible to have a visual signal which is the negative of the signal illustrated in FIG. 3. When the first portion of the visual signal is provided by a printed adhesive layer, it was found that the pattern coverage of the adhesive, i.e. the colored portion, may advantageously represent from about 15% to about 50% of the overall surface of the visual signal. The visual signal may completely cover the layer on which it is applied. The colored portion may thus for example represent from about 20% to about 40% of the surface of the acquisition layer.

FIG. 4 shows an additional example of visual signals, which may be printed on the acquisition layer 52 or present on another layer. The visual signal of FIG. 4 is similar to the visual signal of FIG. 3 with the addition of a pair of longitudinally-extending curved features 270, 271. These curved features each comprise at least one line, and in the example shown at least three lines, that runs lengthwise in the longitudinal direction of the absorbent article, each line being symmetric to its complement across the longitudinal axis. These longitudinally-extending curved features may at least partially correspond to the substantially material-free areas 26, if these are present in the absorbent cores.

Visual Appearance of the Wearer-Facing Side

A color can be characterized by using the CIE L*a*b* scale (measured as indicated in ASTM E1349, see experimental section below). L* represents lightness (0=black, 100=white), a* and b* independently each represent a two color axis, a* representing the axis red/green (+a=red, −a=green), while b* represents the axis yellow/blue (+b=yellow, −b=blue). It is to be understood that the L*a*b* color values are measured on the materials of interest (e.g. on the wearer-facing side of the article to measure the contrast between the differently colored areas).

Using the CIE L*a*b* scale, the visual differences between two colors ("x" and "y") can be conventionally expressed as ΔE*, which is calculated by taking the square root of the sums of the differences to the square for each L*, a* and b* values:

$$\lambda E^* = [(L^*x - L^*y)^2 + (a^*x - a^*y)^2 + (b^*x - b^*y)^2]^{1/2}$$

The phrase a "different color" covers visibly different shades of the same primary color (e.g., dark blue and light blue) or may be completely different color (e.g., blue and grey). Parametrically, two colors can be said to different when they have a ΔE* value of at least 2.0. The colored portion and the non-colored portion of the visual signal as perceived on the wearer-facing side of the article, typically through the topsheet, are advantageously different color according to this definition.

The L*a*b* values of the wearer-facing side of the article on the topsheet can be measured on the finished article directly on a first area of the topsheet corresponding to the first (colored) portion of the visual signal, and a second area of the topsheet corresponding to the second (non-colored) portion of the visual signal. The first area and the second area thus measured should have a different color, having a ΔE* value of at least 2.0, in particular at least 2.5, and optionally at least 3.0 to provide enough contrast between these areas.

The L*a*b* value of the topsheet nonwoven material may also be measured in isolation. For this purpose, several layers of the topsheet are piled up or a layer of topsheet is folded upon itself, so that upon additional layering of the same material or additional folding thereof, the L*a*b* value stay constant. The colored topsheet may in particular have an "a" value ranging from −50 to +15, in particular from −30 to +10, or from −20 to +5 or from −10 to +0. Furthermore, the colored topsheet may have a "b" value from −30 to +10, or from −20 to +5, or from −10 to 0 or from −5 to +0. The colored topsheet may also have a L value from at least 60, such as from 60 to 95, or from 70 to 95, or from 80 to 95.

Topsheet 24

The articles of the present invention comprise a nonwoven colored topsheet. The topsheet may comprise a single layer or may be a multi-layer material with the layers combined by any known means in the art. The topsheet may in particular comprise or consist of a spunbond nonwoven layer. The topsheet is advantageously colored over its entire surface, and typically uniformly colored over its entire surface. Alternatively, it is not excluded that only a portion of the topsheet superposed with the visual signal is colored. Preferably, the topsheet is colored with a single color, typically uniformly colored all over its surface with a single color. The color of the topsheet may be provided by any methods available in the art. The topsheet may be colored after the manufacturing of the nonwoven, but it is simpler to add suitable coloring agents (pigments) to the plastic material, e.g. polyolefin pellets, out of which the fibers of the nonwoven material are made. The topsheet may in particular be a nonwoven material made of synthetic fibers, wherein at least some of the fibers are colored by a pigment introduced in the resin before the nonwoven is made. Various examples of colored topsheets are for example disclosed in EP2,399, 558 (Rinnert et al.). The fibers may be made for example of polypropylene (PP) or may be bicomponent fibers such as PP/PE core/sheath fibers.

The colorants used in the topsheet material may be dyes, organic pigments or inorganic pigments. Typically, the amount of colorant introduced may be of from 0.3%-2.5% by weight of the nonwoven. Alternatively, color may be imparted to the webs by way of impregnation of a colorant into the substrate. Colorants such as dyes, pigments, or combinations may be impregnated in the formation of substrates such as polymers, resins, or nonwovens. For example, the colorant may be added to molten batch of polymer during fiber or filament formation. Pigments can be described as insoluble color matter used in finely dispersed forms. Exemplary organic pigments may include: C.I. Pigment Yellow 1, C.I. Pigment Yellow 3, C.I. Pigment Yellow 13, C.I. Pigment Red 5, C.I. Pigment Red 7, C.I. Pigment Red 12, C.I. Pigment Red 112, C.I. Pigment Red 122, C.I. Pigment Blue 1, C.I. Pigment Blue 2, C.I. Pigment Blue 16, C.I. Vat Blue 4, C.I. Vat Blue 6, or Carbon black. Exemplary inorganic pigments may include carbon black (e.g., Pigment Black 7), iron oxides, ferric oxide black (e.g., Pigment Black 11), chromium oxide, or ferric ammonium ferrocyanide. Exemplary dyes may include: Solvent Yellow 14, Dispersed Yellow 23, Metanil Yellow, Solvent Red 111, Dispersed Violet 1, Solvent Blue 56, Solvent Orange 3, Solvent Green 4, Acid Red 52, Basic Red 1, Solvent Orange 63, or Jet Black. In an example, a topsheet colored in a teal (bluegreen) shade is obtained by using a mixture of Pigment Blue 15 (CAS #147-14-8) and Pigment Green 7 (1328-53-6) in polypropylene. Opacifying agents in particular matting pigments such as titanium dioxide (TiO2) are known to lower the shine appearance of nonwovens and may be comprised in the topsheets of the invention, but these generally white pigments are not considered as coloring agent herein.

The synthetic fibers used to make the topsheet can be any material, such as polyolefins (polypropylene, polypropylene copolymers, polyethylene, polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Non-synthetic fibers such as cellulose fibers may also be used.

Preferably, the topsheet is made of a nonwoven material made of a polyolefin, such as polyethylene, polypropylene or mixtures thereof. The topsheet may be a multilayer nonwoven web, i.e. a laminate. The laminate may comprise spunbond layer(s) (S), and/or meltblown layer(s) (M), and/ or carded layer(s) (C). Suitable laminates include, but are not limited to, SS, SSS, SMS or SMMS. The topsheet may in particular be a spunbond nonwoven material, such as a mono layer spunbond (S) comprising PP fibers, or a dual layer spunbond (SS) or a nonwoven material comprising more than two layers, such as a spunbond nonwoven with three layers (SSS).

The topsheet useful in the invention may have a range of basis weight. Advantageously, the basis weight of the nonwoven can be equal or below 30 gsm, in particular equal or below 25 gsm. For performance reasons, it is difficult to use a topsheet having a basis weight of below 10 gsm. The colored topsheet may have for example a basis weight of from 10 gsm to 20 gsm, or from 12 gsm to 18 gsm.

The topsheet is also partially transparent, so that a visual signal underneath is at least partially visible for the user of the article though the garment-facing side of the article. Due to the subtractive effect of the colored topsheet, the colored portion of the visual signal will appear darker through the topsheet and the non-colored portion of the visual signal will appear to have the color of the topsheet. This provides the wearer-facing side of the article with a dual color appearance. The opacity of the topsheet can be measured using the method indicated further below. The topsheet advantageously have an opacity index of at least 28%. In particular the opacity index may range from 28% to 75%, in particular from 28% to 50%, or from 28% to 43%, or from 29% to 35%. If the opacity is too low, the topsheet material may appear too thin and the desired dual color visual effect is not provided satisfactorily. If the opacity it too high, the material may be too opaque and the visual signal under the topsheet may be difficult to discern and not sufficiently visible.

Topsheet Bonding Pattern

The topsheet advantageously comprises a nonwoven having a pattern of thermal bonds. By "thermal bonds", it is meant discrete areas of the nonwoven wherein the fibers are melted and fused, i.e. heated to a temperature above their melting point, to improve the structural integrity of the nonwoven. The thermal bonds (also called fusion bonds) can be typically provided by heat bonding or by a combination of pressure and heat bonding. Typically the nonwoven is passed directly after its formation between two calender rolls with a roll comprising protrusions having a flat surface corresponding to the pattern of thermal bonds desired. At least one of the calender rolls may be heated.

Various bonding patterns may be used. WO2011/163046A1 (Rinnert et al.) for example discloses a colored topsheet having a basis weight of from about 12 gsm to about 18 gsm and comprises a plurality of generally circular thermal bonds, wherein each of said points has a surface area of from about 2 mm$^2$ to about 5 mm$^2$ and wherein the cumulated surface area of the plurality of thermal bonds is from about 10% to about 25% of the total surface area of the topsheet.

Other exemplary bonding patterns which may be used with the colored topsheet of the invention are shown in FIGS. 5-6 and FIGS. 9-10. These bonding patterns are believed to reduce the occurrence of fiber ends sticking out of the surface of the nonwoven, a phenomenon also referred to as fuzz. It is believed that fuzz is caused by the fibers being insufficiently bonded by the thermal bonds, in particular in that some fibers are bonded by a single bonding point along their length. It is believed that to reduce fuzz, a maximum number of the fibers should be bonded by at least two thermal bonds so that the extremities of the fiber have less chance to stick out of the surface of the nonwoven. The patterns illustrated comprise elongated rounded thermal bonds that are believed to be more likely than generally circular thermal bonds to attach a given fiber at two thermal bonds.

It was found that the thermal bonds can be more transparent in multi-lobal (e.g. trilobal) fiber nonwovens than the unbonded area of the nonwoven, and thus improve the visibility of the underlying visual signal. The opposite effect may be found using round fibers to form the nonwoven. Having too much thermal bonds on the surface of the topsheet may on the other hand have a negative effect on the softness of the topsheet. The cumulated area of the plurality of thermal bonds may in particular represent from 15% to 30%, or from 17% to 28%, or from 19% to 27%, or from 20% to 26% of the total surface area of the topsheet on which the bonding pattern is applied. The thermal bonds may generally have the same dimensions as in Rinnert et al., or the bonds may advantageously comprise bonds having different dimensions in particular different areas as shown in FIGS. 5-6 and FIG. 9-10. At least some of the plurality of thermal bonds may for example a surface area of from 1 mm$^2$ to 6 mm$^2$. This range was found to provide good anti-fuzz properties, good visibility of the visual signal underneath, while keeping the nonwoven soft to the skin.

Figure 5:
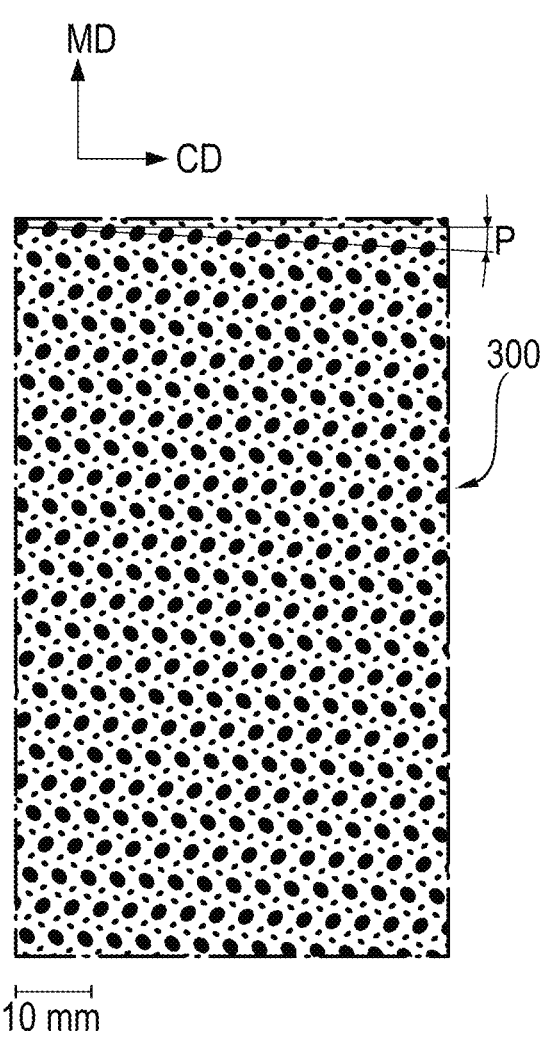
FIG. 5 shows of an exemplary bonding pattern for a topsheet nonwoven at a scale 1:1 comprise thermal bonds of different sizes.
Figure 6:
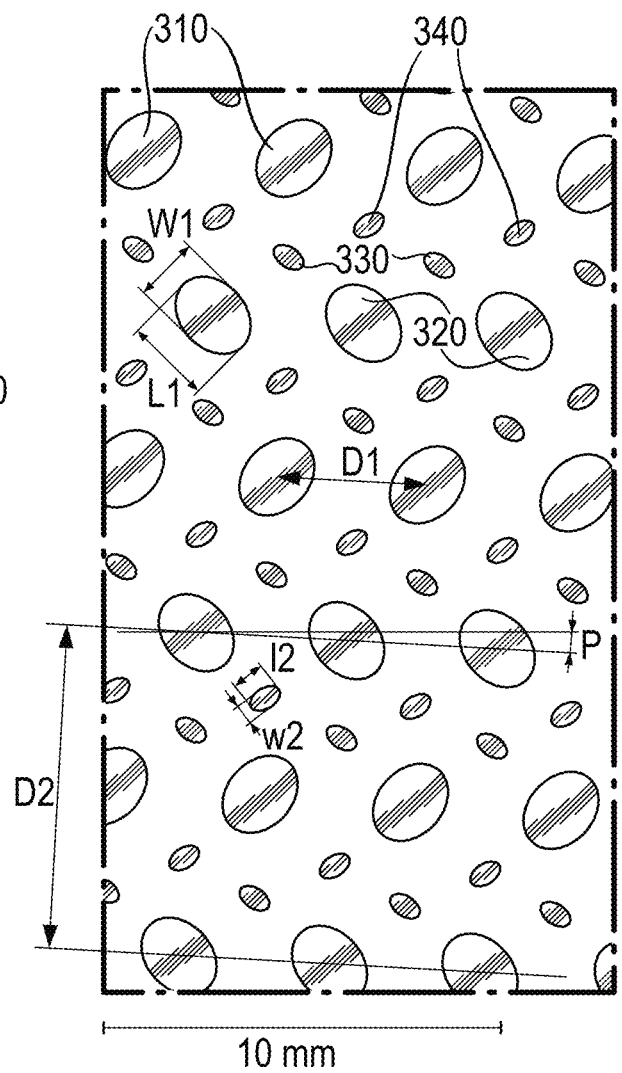
FIG. 6 shows a close-up of the bonding pattern of FIG. 5 at a scale 5:1.

FIG. 5 illustrates a bonding pattern 300 for the nonwoven topsheet having thermal bonds of different sizes and orientation. FIG. 5 is at a scale of 1:1, while FIG. 6 is a close-up view at a scale of 5:1. The nonwoven material extends in a machine direction (MD) and a perpendicular cross-machine direction (CD). The machine direction is the direction along which the web is continuously formed, for example by a spunbonding process as is known in the art. The machine direction is the continuous or "long" direction of the web, along which the web may be rolled in a roll before being converted in an absorbent article converting line. The machine direction of the web is thus typically the same direction as the longitudinal direction 80 of the finished article. The thermal bonding pattern is typically applied to the nonwoven web immediately after the nonwoven web has been formed.

The bonding pattern 300 illustrated in FIGS. 5-6 comprises larger elongated thermal bonds 310, 320 which have a major dimension L1 measured along a major direction and a minor dimension W1 measured along a minor direction perpendicular to the major direction, and smaller elongated thermal bonds 330, 340 having a major dimension l2 measured along a major direction and a minor dimension w2 measured along a minor direction perpendicular to the major direction. The major dimension L1 of the larger bonds may be at least 50%, in particular at least 75% or at least 100%, higher than the major dimension l1 of the smaller bonds. The bonds are generally rounded with no sharp angles, and in particular may be elliptical. The major dimension L1 of the larger bonds may for example be at least 1.50 mm, in particular at least 1.75 mm or at least 2.00 mm, and the major dimension l1 of the smaller bond may be less than 1.50 mm, in particular less than 1.25 mm, or less than 1.00 mm. The larger bonds may have an individual surface ranging from 1.0 mm$^2$ to 9.0 mm$^2$ and the smaller bonds have an individual surface ranging from 0.12 mm$^2$ to 1.4 mm$^2$.

At least some of the larger elongated thermal bonds 310, 320 may have a ratio L1/W1 of the major dimension to the minor dimension of from 1.05 to 2.0, and at least some of the smaller elongated bonds 330, 340 have a ratio of the major dimension to the minor dimension of from 1.10 to 2.5. As can be seen in FIG. 6, the larger bonds may comprise at least two types of larger bonds, wherein the first type 310 and the second type 320 of larger bonds have a different major direction, in particular wherein the two types of larger bonds are oriented symmetrically relative to the machine direction (MD). The different types of larger bonds may have the same individual area as shown or different surfaces but it is not excluded that they may be different. Similarly the smaller bonds comprise at least two types of smaller bonds, wherein the first type 330 and the second type 340 of smaller bonds have a different major direction, in particular wherein the two types of smaller bonds are oriented symmetrically relative to the machine direction (MD). The different types of smaller bonds may have the same individual area as shown, or they may have different areas. The bonding pattern may comprise at least three, in particular four or more different type of bonds 310, 320, 330, 340, wherein each type of bonds is defined by size and orientation of its major direction.

The thermal bonds may be arranged in rows generally orientated parallel to the cross-machine direction, taking into account the pitch angle P. The pitch angle measures the angle between the rows and the cross-machine direction (CD), any may typically range from 0 to 10 degrees relative to the cross-machine direction (CD), in particular between 1 and 5 degrees. Having a non-zero pitch angle improve the properties of the bonding pattern by ensuring two consecutive rows of the same type of bonds are slightly shifted in CD direction and thus helps during the manufacturing process maintaining an about constant pressure between the calender rolls. The bonds in a row may be all of the same type. The repeat in width distance center-to-center D1 of two bonds of the same type (same size and same orientation) in a given row may for example range from 2.0 mm to 8 mm. The repeat in height distance D2 between two rows of the bonds of the same type may be for example from 4.0 mm to 16 mm. The same or different distances may be used for each row having bonds of the same type.

Exemplary dimensions for the bonding pattern of FIGS. 5-6 are as follow: L1=2.25 mm, W1=1.8 mm, l2=0.88 mm, w2=0.52 mm, D1=4.09 mm, D2=8.63 mm, P=3°. The bonding pattern is applied over the whole of the surface of the nonwoven. The bonding area represents 22.1% of the surface of the topsheet. The bonding pattern comprises on average 17 thermal bonds per cm$^2$. The larger thermal bonds have an individual surface of 3.18 mm$^2$ and the smaller thermal bonds have an individual surface of 0.36 mm$^2$.

Figure 7:
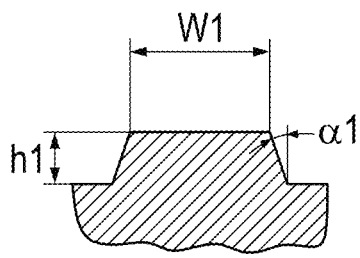
FIG. 7 is a schematic cross-section of the protrusion of a calender roll for the larger bonds at a scale 10:1.
Figure 8:
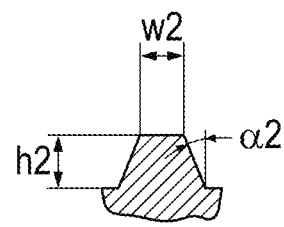
FIG. 8 is a schematic cross-section of the protrusion of a calender roll for the smaller bonds at a scale 10:1.

The thermal bonds shown can be obtained by passing the nonwoven web through two calender rolls, at least one of the calender rolls having bonding protrusions. The protrusions are illustrated by FIGS. 7 and 8 showing cross-sections of the protrusions in their minor directions at a scale of 10:1. FIG. 7 illustrates a protrusion for providing the larger thermal bonds 310, 320, while FIG. 8 illustrates a protrusion for providing the smaller thermal bonds 330, 340. The protrusions have a height h1, h2 (also referred to as engraving depth), with typically h1 being equal to h2, and the side walls of the protrusions extend from the surface of the roll at angles α1, α2, with typically al being equal to α2. In the specific example shown, h1=h2=0.68 mm, α1=α2=22°.

Figure 9:
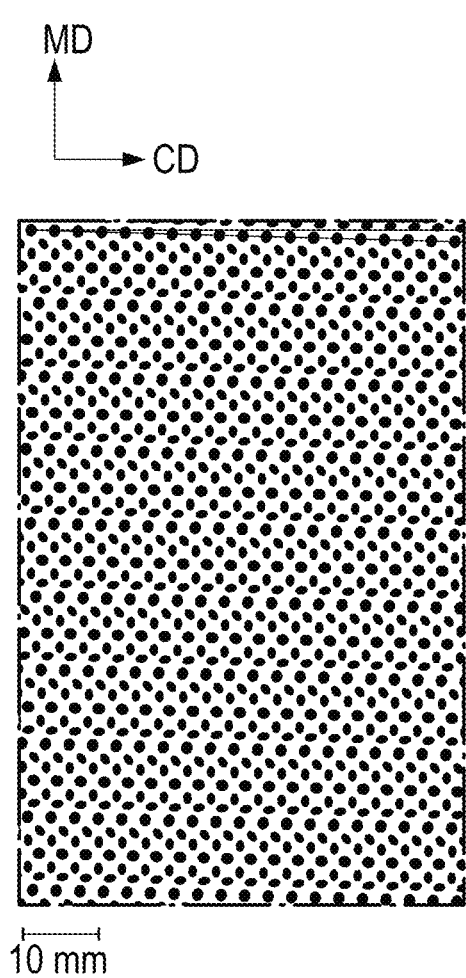
FIG. 9 shows another exemplary bonding pattern at a scale 1:1.
Figure 10:
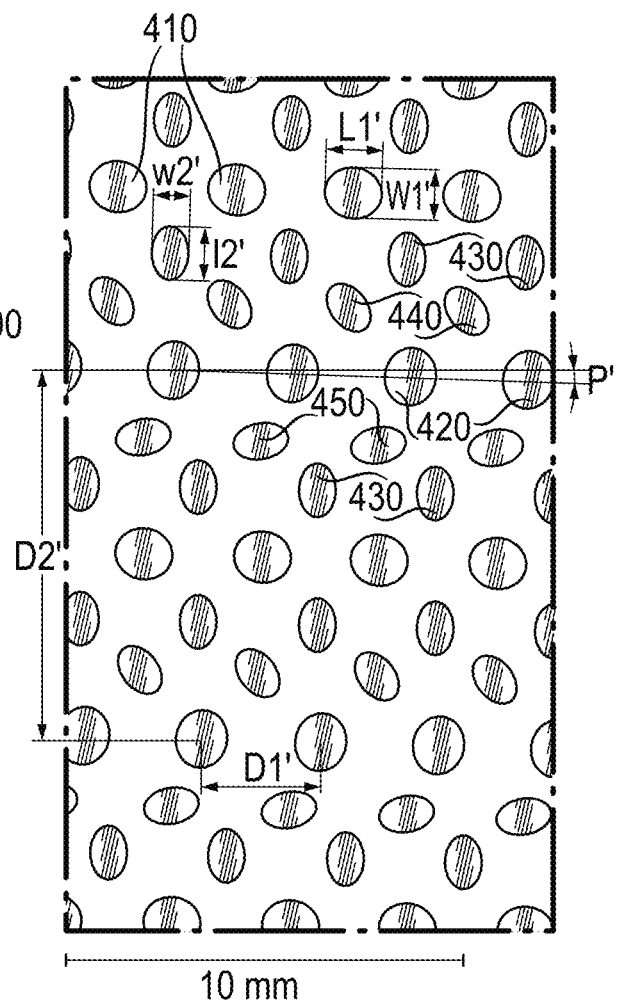
FIG. 10 shows a close-up at a scale 5:1 of the bonding pattern of FIG. 9.

FIGS. 9-10 shows an alternative improved bonding pattern 400 that may be used to bond the fibers of a colored nonwoven topsheet of the invention. FIG. 9 is at a scale of 1:1, while FIG. 10 is a close-up view at a scale of 5:1. In general it was found that a bonding pattern may comprise at least three different types of elongated thermal bonds, defined by different individual surfaces and/or major directions. The previous example had 4 types of bonds: two larger types of bonds 310, 320 with different directions and two smaller bonds 330, 340 with different directions. The bonding pattern illustrated FIGS. 9-10 comprise five types of thermal bonds: two larger bonds 410, 420 having the same individual area and different directions, and three smaller bonds 430, 440, 450 having the same individual areas and different directions.

The larger elongated thermal bonds 410, 420 have a major dimension L1' measured along a major direction and a minor dimension W1' measured along a minor direction perpendicular to the major direction, and the smaller elongated thermal bonds 430, 440, 450 having a major dimension l2' measured along a major direction and a minor dimension w2' measured along a minor direction perpendicular to the major direction. The bonds may be generally elliptical in shape, and some bonds (not represented) may be circular. As visually recognizable, the size differences between the larger and the smaller bonds is less than for the bonding pattern of FIGS. 5-6, however the bonds are orientated in more directions and also provide a benefits in terms of improved bonding of the fibers and reduced fuzz. The major dimension L1' of the larger bonds may be for example from 5% to 50% higher than the major dimension l1' of the smaller bonds. The major dimension L1' of the larger bonds may be for example at least 1.0 mm, in particular at least 1.2 mm or at least 1.4 mm and up to 4 mm and the major dimension l2' of the smaller bonds may be for example at least 0.6 mm, in particular at least 0.8 mm or at least 1.0 mm and up to 3 mm.

The larger bonds 430, 440 may for example have an individual area ranging from 0.8 mm$^2$ to 3.6 mm$^2$ and the smaller bonds have an individual surface ranging from 0.6 mm$^2$ to 1.8 mm$^2$. The smaller bonds may have a more elongated appearance than the larger bonds. For example at least some of the larger elongated thermal bonds may have a ratio L1'/W1' of the major dimension to the minor dimension of from 1.05 to 1.5, and at least some of the smaller elongated bonds have a ratio l2'/w2' of the major dimension to the minor dimension of from 1.10 to 2.0. As can be seen in FIG. 10, the larger bonds may comprise at least two types of larger bonds, wherein the first type 410 and the second type 420 of larger bonds have the same surface area and a different major direction. The smaller bonds may comprise at least two or three types of smaller bonds. The different types of smaller bonds may have the same individual surface with different major direction, as shown, or they may have different surfaces and/or different major directions. The bonding pattern may comprise at least three, in particular at least four or at least five or more bonds 410, 420, 430, 440, 405 of different types, wherein the types of bonds differ in size and/or orientation of the major direction.

The bonds may be arranged in rows generally orientated parallel to the cross-machine direction, taking into account the pitch angle P', wherein the bonds in a row may be all of the same type. The pitch angle P' may be in the same range as indicated previously for FIGS. 5-6. The repeat in width distance center-to-center D1' of two bonds of the same type (same size and same orientation) may for example range from 2.0 mm to 8 mm. The same or different distances may be used between any two bonds of the same type. The repeat in height distance D2' between two rows of bonds of the same type may be for example from 6.0 mm to 20 mm. The same or different distances may be used between all the rows of the bonds of the same type.

Exemplary dimensions for the bonding pattern of FIGS. 9-10 are as follow: L1'=1.6 mm, W1'=1.4 mm, l2'=1.5 mm, w2'=1 mm, D1'=3.29 mm, D2'=10.3 mm, P'=2°. The bonding area is applied over the whole of the surface of the nonwoven. The bonding area represents 24.2% of the surface of the topsheet. The bonding pattern comprises on average 17.6 thermal bonds per cm². The larger thermal bonds have an individual surface of 1.76 mm² and the smaller thermal bonds have an individual surface of 1.18 mm²

Figure 11:
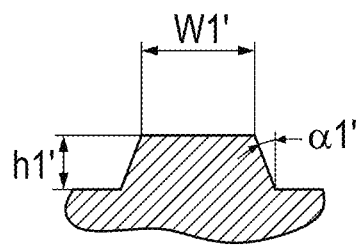
FIG. 11 is a schematic cross-section of the protrusion of a calender roll for the larger bonds at a scale 10:1.
Figure 12:
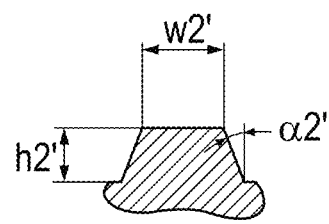
FIG. 12 is a schematic cross-section of the protrusion of a calender roll for the smaller bonds ata scale 10:1.

FIGS. 11 and 12 show cross-sections of protrusions that may be used to thermally emboss the nonwoven with the bonding pattern 400 in their minor directions at a scale of 10:1. FIG. 11 illustrates a protrusion for providing the larger thermal bonds 410, 420 while FIG. 12 illustrates a protrusion for providing the smaller thermal bonds 430, 440, 405. The protrusions have a height h1', h2' (also referred to as engraving depth), with typically h1' being equal to h2', and the side walls of the protrusions extend from the surface of the roll at angles α1', α2', with typically α1' being equal to α2'. In the specific example shown, h1'=h2'=0.68 mm, α1'=α2'=22°.

Acquisition Layer 52

The absorbent article may advantageously comprise an acquisition layer 52, whose function is to quickly acquire the fluid away from the topsheet so as to provide a good dryness for the wearer. The acquisition layer is typically placed directly under the topsheet. If present, a distribution layer may be present between the acquisition layer and the absorbent core.

This acquisition layer, sometimes referred to as secondary topsheet, may for example be a through air-bonded carded web ("TABCW") but many other alternatives material are known in the art and may be used instead. "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). The TABCW material provides a low density, lofty web. The web may in particular have a specific weight basis level at about 15 to about 70 gsm (gram per m²). The TABCW material can for example comprise about 3 to about 10 denier staple fiber. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

The acquisition layer 52 may also be or comprise a nonwoven material, for example a SMS or SMMS material, comprising a spunbonded, a melt-blown and a further spunbonded layer, or alternatively a carded chemical-bonded nonwoven. The nonwoven acquisition layer may in particular be latex bonded. Exemplary acquisition layers are disclosed in U.S. Pat. No. 7,786,341 (Schneider et al.). Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/148684 (Cramer et al.) and US2005/008839 (Cramer et al.).

The acquisition layer may be stabilized by a latex binder, for example a styrene-butadiene latex binder (SB latex). The latex may be obtained by known process, for example as disclosed in EP149880 (Kwok) or US 2003/0105190 (Diehl et al.). The binder may for example be present in the acquisition layer 52 in excess of about 12%, about 14% or about 16% by weight of the layer. SB latex is available under the trade name GENFLO™ 3160 (OMNOVA Solutions Inc.; Akron, Ohio).

A further acquisition layer (not shown) may be used in addition to the first acquisition layer described above. For example a tissue layer may be placed between the first acquisition layer 52 and a distribution layer 54. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Although not shown in the drawings, it is possible and advantageous to bond the topsheet directly or indirectly to the underlying acquisition layer. These layers may be bonded by any known bonding means, such as slot gluing, spiral gluing, fusion point bonding, or otherwise attached.

Distribution Layer 54

A distribution layer 54 may be optionally present between the core 26 and the acquisition layer 52. The function of a distribution layer is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 to 0.25 g/cm³, in particular from 0.05 to 0.15 g/cm³ measured at 0.30 psi (2.07 kPa). The distribution layer may also be a material having a water retention value of from 25 to 60, preferably from 30 to 45, measured as indicated in the procedure disclosed in U.S. Pat. No. 5,137,537. The distribution layer may typically have an average basis weight of from 30 to 400 g/m², in particular from 100 to 300 g/m².

The distribution layer may for example comprise at least 50% by weight of crosslinked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance against the compression in the product packaging or in use conditions, e.g. under baby weight. Exemplary chemically cross-linked cellulosic fibers suitable for a distribution layer are disclosed in U.S. Pat. Nos. 5,549,791, 5,137,537, WO 95/34329 or US2007/118087. The distribution layer may be applied homogenously in a rectangular shape, or may be applied at different basis weight along its length and may be, as illustrated, rounded towards the back of the article. This may provide for a more efficient usage of the distribution material. Such a profiled distribution of the distribution layer is for example disclosed in WO2014/093323 (Bianchi et al.).

Absorbent Core 28

As used herein, the term "absorbent core" refers to the component of the article which has the most absorbent capacity of all the components of the absorbent article, and which comprises all, or at least the majority of, superabsorbent polymer (SAP). The absorbent core comprises an absorbent material typically enclosed in a core wrap and is used to absorb and retain most of the liquid exudates. The terms "absorbent core" and "core" are herein used interchangeably.

An exemplary core 28 is represented in FIG. 2 in a dry state and in isolation. Absorbent cores can typically be laid flat on a surface, but of course they can also be laid on a non-flat surface for example a drum during their making process or stored as a continuous roll of stock material before being converted into an absorbent article. The absorbent core typically extends in a longitudinal direction parallel and contiguous to the longitudinal axis 80 of the absorbent article and a transversal direction perpendicular to the longitudinal direction. Unless otherwise indicated, dimensions and areas disclosed herein apply to the core in this flat-out configuration. The same applies to the absorbent article in which the core is integrated.

The absorbent core as delimited by the core wrap 16, 16' is typically rectangular with a front end, a back end and two longitudinally extending side edges. The core has a width as measured in the transversal direction and a length as measured in the longitudinal direction, from edge to edge including the region of the core wrap which does not enclose the absorbent material. The front end and back end may or may not be sealed. The width and length of the core may vary depending on the intended usage. For baby and infant diapers, the width may for example in the range from 40 mm to 200 mm and the length from 100 mm to 500 mm, as measured along the longitudinal axis of the core. In case the core is not rectangular, the maximum dimension measured along the transversal and longitudinal direction can be used to report the length and width of the core.

The core wrap comprises a top side 16 oriented towards the wearer-facing side of the article and a bottom side 16' oriented towards the garment-facing side of the article. The core wrap may be formed of a single web wrapped around the absorbent material with one longitudinal seal to attach overlapping portions of the substrate to each other. The top and bottom sides may also be formed by two separate substrates which may be the same or different material (the top layer being for example hydrophillically treated). These two substrates may be partially attached together in particular by gluing the flaps of the wider material to the other material to form two so-called C-wrap seals extending longitudinally of the core. This gluing may be for example provided by two slots of glue. Independent of the construction, the core wrap material may be any suitable material used in the field, typically a nonwoven web, such as a laminate comprising spunbond ("S") or meltblown ("M") layer. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US 2011/0319848A1 and US2011/0250413A1. It is also not excluded that the core wrap may be partially or entirely formed by layers having an additional function such as the backsheet, the topsheet or an acquisition layer.

The absorbent material 60 in the core 28 may typically comprise fibers mixed with superabsorbent polymer particles. The fibers may typically comprise wood pulp (cellulose) fibers optionally mixed with synthetic fibers. The absorbent material typically comprises from 50% to 90% of superabsorbent polymers (herein abbreviated as "SAP" also referred to as absorbent gelling material) by weight of the absorbent material. The absorbent material may for example comprise at least 55% superabsorbent polymers by weight of the absorbent material, in particular from 60% to 90% superabsorbent polymers by weight of the absorbent material, in particular from 65% to 85% superabsorbent polymers by weight of the absorbent material. It is not excluded that higher amount of SAP may be present. The absorbent material may also comprise little or no cellulose fibers (so called airfelt-free cores). These airfelt-free absorbent cores may comprise superabsorbent polymers immobilized by one or more adhesives. The SAP may also be immobilized within pockets formed e.g. by ultrasonic bonding. Examples of airfelt-free cores are disclosed in WO95/11652 (Tanzer), U.S. Pat. No. 6,790,798 (Suzuki), WO2008/155699 (Hundorf), or WO2012/052172 (Van Malderen).

The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example. It is not excluded that higher amount of SAP may be present, and in some cases it may be possible that the absorbent material comprise little or no cellulose fibers (so called airfelt-free cores).

The absorbent material 60 defines an absorbent material deposition area, as seen as from above within the plane of the core. The absorbent material deposition area may be rectangular as represented in FIG. 2, or it may be shaped, i.e. not rectangular for example having recesses along the longitudinal edges of the deposition area. The shape of the deposition area may thus be described a sand-hour or dog-bone shape, but other shapes can also be used such as a "T" or "Y". In this way, the absorbent material deposition area may have a relatively narrow width in an area of the core intended to be placed in the crotch region of the absorbent article. Having the width of the absorbent material deposition area maximum at the front edge and/or at the back edge of the absorbent material area, and minimum at a longitudinal position between the front edge and the back edge of the absorbent material area may provide better wearing comfort for the wearer.

Absorbent cores with slits or grooves sometimes referred to as channels have also been proposed, typically to increase the fluid acquisition properties of the core or to act as a folding guide. The absorbent cores may comprise at least one, and advantageously at least one pair, of longitudinally-extending substantially material free areas 26. The absorbent core may in particular comprise a pair of channels symmetrically placed relative to the longitudinal axis, but it is not excluded that only one channel may be present, or more than a pair of channels. By "substantially free" it is meant that in the material free areas the basis weight of the absorbent material is at least less than 25%, in particular at least less than 20% or less than 10%, of the average basis weight of the absorbent material in the rest of the absorbent material deposition area. In particular there can be no absorbent material in these areas. Minimal amount such as involuntary contaminations with absorbent material that may occur during the making process are not considered as absorbent material. The substantially material free areas 26 are advantageously surrounded by the absorbent material, which means that these areas do not extend to any of the edge of the deposition area 8 of the absorbent material. Typically, the smallest distance between a material free area and the closest edge of the absorbent material deposition area 8 is at least 5 mm.

WO2012/170778 (Rosati et al., see also WO2012/170779, WO2012/170781 and WO2012/170808) discloses absorbent structures that comprise superabsorbent polymers, optionally a cellulosic material, and at least a pair of longitudinally-extending absorbent material free areas. The top side 16 of the core wrap may be attached to the bottom side 16' of the core wrap through the substantially material free areas by one or a plurality of bonds. Various bonding means can be used such as ultrasonic, heat (fusion), mechanical or adhesive bonding. Ultrasonic bonding may be particular useful in terms of reduced raw material usage and strength of the bond. When the absorbent material swells upon absorbing a liquid, the bonds remain at least initially attached. The absorbent material swells in the rest of the core, so that the core wrap forms more marked three-dimensional channels along each area 26 where the bonds are present. This can help providing a quicker fluid acquisition speed and a better utilization of the absorbent capacity of the core. The three-dimensional channels can also provide a deformation of an overlying layer such as a fibrous distribution layer 54 and provide corresponding ditches in the overlying layer (see WO2014/200794A1, Bianchi et al.).

As the absorbent core absorbs liquid, the depressions formed by these material free areas will become deeper and more apparent to the eye and the touch from the exterior of the article as the backsheet and topsheet are pushed outwardly by the expending absorbent material. If the core wrap bonds through the material free areas are sufficiently strong and the level of SAP is not too high, it is possible that the channel bonds remain permanent until complete saturation of the absorbent material. On the other hand, the channel bonds may in some cases also restrict the swelling of the absorbent material when the core is substantially loaded. The bonds may also be designed to open in a controlled manner when exposed to a large amount of fluid. The bonds may thus remain substantially intact at least during a first phase as the absorbent material absorbs a moderate quantity of fluid. In a second phase the channel bonds can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of the channel bonds can be controlled for example by varying the number and intensity of the point bonds attaching the two sides of the core wrap and/or the distribution of the superabsorbent material, as more absorbent material will usually causes more swelling and will put more pressure on the bond. The extensibility of the material of the core wrap may also play a role.

The channel-forming areas 26 may in particular have a length L' projected on the longitudinal axis 80 that is at least 10% of the length L of the absorbent article, in particular from 20% to 80%. The channels 26 may be for example have a length L' of at least 2 cm as measured on the longitudinal axis, or at least 4 cm, 6 cm, 8 cm, or 10 cm, and for example up to 40 cm, or 30 cm. Shorter channels may also be present in the core, for example in the back region or the front region of the core, as seen for example in the Figures of WO2012/170778. Each area 26 may have a width Wc along at least part of its length which is at least 2 mm, or at least 3 mm or at least 4 mm, up to for example 20 mm, or 16 mm or 12 mm. The width Wc of each channel 26 may be constant through substantially its whole length or may vary along its length. The channels may be straight and longitudinally oriented parallel to the longitudinal axis. The channels may also be inwardly curved (concave) towards the longitudinal axis, as for example represented in FIG. 2.

Waistband 48

As illustrated in FIG. 1, the article 20 also has an elastic back waistband 48 extending transversally adjacent the back waist edge 12 of the article. Such waistbands (also called elastic waist features) may typically comprise a nonwoven substrate and a plurality of elastic strands 49 transversally orientated. Typical waistbands comprise extruded strand elastomer between two layers of spunbond nonwoven; e.g. using PP fibers or bi-component core/sheath PE/PP or PE/PET fibers. Other types of substrates may be used if desired. Spandex (=Elastane or Lycra®) strands may also be used as elastics between the nonwovens. Other executions of applied waistband consist of elastics stretched in the process and applied transversely to the length of the articles directly sandwiched in between some wearer-facing and some garment-facing material.

The waistbands in cooperation with the other features of the invention results in absorbent articles having increased comfort, fit, and improved leakage performance for the wearer. As indicated previously, it was found that absorbent core with longitudinally-extending channels may provide an increased rigidity in the longitudinal direction when the absorbent material has swollen and presses against the walls of the core wrap defining the channels. This may create further gaps towards the back edge of the article. The present invention delivers an absorbent article having improved gap closure in at least the back waist region of the absorbent article using the combination of the stretchable waistband and the stretchable back ears. The article may comprise, in addition to the back waistband 48, a front elasticized waistband (not represented). In the following, the description referring to the back waistband may also refer independently to the front waistband, unless specifically indicated otherwise. "Stretchable", "elastic", "elastically extensible", and "elasticized" refer herein to the property of a material and/or an element of a diaper or other disposable absorbent article whereby the material and/or the element can be elongated to at least 150% of its original un-stretched length without rupture or catastrophic failure upon the application of tensioning force and will substantially return to its original length or near its original length after the tension is released.

The waistband 48 typically comprises a laminate of a nonwoven and several elastic strands 49 that are combined with the chassis under some tension. Elastic strands are the most cost effective way to get stretch that exhibits little relax or set over time. Nonwovens are preferred for the exterior of the waist band material because it is breathable and softer than film alternatives, but films may also be used as waistband material. The waistband laminate may further comprise any number of strands are as desired, for example from 2 elastic strands to 40 elastic strands, for example from 4 elastic strands to 26 elastic strands. It is also known that when strands of elastic are combined under strain with other often non-extensible materials and then allowed to relax, they will create a laminate that has gathers of a certain frequency and a resulting basis weight that is higher than the starting materials laid flat. Non-limiting examples of back and front waistbands can be found in WO2012/177400 and WO2012/177401 (Lawson), and U.S. Pat. Nos. 4,515,595, 4,710,189, 5,221,274 and 6,336,922 (VanGompel et al.).

The waistband is generally placed adjacent the corresponding waist edge of the article. The distance between the waistband and the edge of the article may be in particular less than 40 mm, in particular the distance between the (back) waistband and the (back) edge of the article may be from 0 mm to 30 mm. The waistband may be attached to the article with adhesive, mechanical bonds, or any other forms of attachment known in the art.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g. urine). The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film may include at least about 20 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 g/m²/24 hours.

Back Ears 40, Fastening Tabs 42 and Landing Zone 44

The absorbent article may comprise stretchable back ears 40 each comprising attached thereto at least one fastening tab 42. The fastening tabs 42 can be releasably engaged with the landing zone 44 disposed on the garment-facing side of the article adjacent the front edge of the article. The landing zone 44 may be a discrete material adhered to the topsheet but it is not excluded that the outer surface of the backsheet as a whole may function as a landing zone over its all surface. The back ears, fastening tabs and the landing zone may be any standard components known in the art. On the other hand, articles presented to the user in closed form such as pants typically do not comprise back ears releasably engageable with a landing zone but will comprise pre-formed side seals.

The ears may be an integral part of the chassis, such as formed from the topsheet 24 and/or backsheet 26 as side panel but more typically, as represented on FIG. 1, the ears may be separate elements attached by gluing, heat embossing, and/or pressure bonding to the rest of the article. The back ears 40 may be stretchable to facilitate the attachment of the fastening tabs 42 to the landing zone 44 and maintain the taped diapers in place around the wearer's waist. The stretchable back ears 40 also provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract. The back ears may in particular be a stretchable laminate comprising an elastomeric film sandwiched between two nonwoven layers. The nonwoven layer may for example be a spunbond nonwoven (e.g. PP or PE/PP bico fibers) and the film a SBC/POE mix. The basis weight of the laminate may typically range from 50 gsm to 200 gsm, for example 110 gsm or 150 gsm. The nonwoven may typically have a nonwoven basis weight ranging from 20-30 gsm and the film's basis weight may typically range from 35-45 gsm.

The fastening tabs 42 are typically a plastic material attached to the back ears and may for example comprise "Velcro-type" hooks that can releasably engage with loops disposed on the landing zone 44. Many different systems have been suggested in the art. Some exemplary surface fastening systems are disclosed in U.S. Pat. No. 3,848,594 entitled "Tape Fastening System for Disposable Diaper" issued to Buell; U.S. Pat. No. 4,662,875 issued to Hirotsu et al.; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard; U.S. Pat. No. 4,946,527 entitled "Pressure-Sensitive Adhesive Fastener And Method of Making Same" issued to Battrell on Aug. 7, 1990; U.S. Pat. Nos. 5,151,092 and 5,221,274. An exemplary interlocking fastening system is disclosed in U.S. Pat. No. 6,432,098 entitled "Absorbent Article Fastening Device" in the names of Kline et al.

The landing zone 44 may for example be a pattern-unbonded nonwoven fabric as disclosed in U.S. Pat. No. 5,858,515 and comprising a first nonwoven web having a fibrous structure of individual fibers or filaments. The nonwoven web may have a bulk of at least about 10 mils and a basis weight of at least about 20 grams per square meter. The nonwoven web may have on a surface thereof a pattern of continuous bonded areas defining a plurality of discrete unbonded areas formed by application of heat and pressure; with a percent bond area of from about 25 percent to about 50 percent; the individual fibers or filaments within the discrete unbonded areas having at least a portion thereof extending into and bonded within said continuous bonded areas.

Cuffs 32, 34

The absorbent articles may typically further comprise components that improve the fit of the article around the legs of the wearer, in particular a pair of barrier leg cuffs 34 and gasketing cuffs 32 (not shown in FIG. 2). The barrier leg cuffs 34 may each be formed by a piece of material, typically a nonwoven, that can be partially raised away and thus stand up from the plane defined by the topsheet. The material of the barrier leg cuffs may thus comprise a first portion flush with the topsheet and limited inwardly by a proximal edge. This first portion may be attached to the topsheet and/or backsheet with an intermittent or continuous thermal bond and/or a glue bond. The barrier leg cuffs 34 further comprise a free-standing portion limited by a distal edge, which in use fits at the junction of the thighs with the torso of the wearer, at least in the crotch region of the article. The barrier leg cuffs can provide improved containment of liquids and other body exudates approximately at the junction of the torso and legs of the wearer. Typically, the barrier leg cuffs are formed from a separate material joined to the rest of the article, in particular to the topsheet, but it is not excluded that the barrier leg cuffs can be integral with (i.e. formed from) the topsheet or the backsheet, or any other layer, for example the bottom layer of the core wrap. Typically the material of the barrier leg cuffs may extend through the whole length of the article but is further bonded to the topsheet towards the front edge and back edge of the article so that in these sections the barrier leg cuff material remains flush with the topsheet (tack bonds not shown in FIG. 1 for readability). Each barrier leg cuff 34 typically comprises one, two or more elastic strings 35 close to the free standing terminal edge.

In addition to the barrier leg cuffs 34, the article may typically comprise gasketing cuffs 32, which may be present as part of the chassis of the absorbent article. The gasketing cuffs may be at least partially enclosed between the topsheet and the backsheet, or the barrier leg cuffs and the backsheet. The gasketing cuffs may be placed transversally outward relative to the proximal edge 65 of the barrier leg cuffs 34. The gasketing cuffs 32 can provide a better seal around the thighs of the wearer. Usually each gasketing cuff 32 will comprise one or more elastic string or elastic element(s) 33 embedded within the chassis of the diaper, for example between the topsheet and backsheet in the area of the leg openings. These elastic elements 33 may, independently or in combination with the elastics 35 of the barrier leg cuffs, help shaping the absorbent article into a basin shape when put in place on and being worn by the wearer.

Various cuff constructions have been disclosed for in the art and may be used in the present invention. U.S. Pat. No. 3,860,003 describes a disposable diaper which provides a contractible leg opening having a side flap and one or more elastic members to provide gasketing cuffs. U.S. Pat. Nos. 4,808,178 and 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. More recently, WO2005/105010 (Ashton) discloses a dual cuff system made of a continuous cuff material. All or a portion of the barrier leg and/or gasketing cuffs may be treated with a lotion.

Method of Making the Article—Relations Between the Layers

The absorbent articles of the invention may be made by any conventional methods known in the art. In particular the articles may be hand-made or industrially produced at high speed. The individual component of the article may be made by conventional means or as indicated previously in the description of the component. More generally, adjacent layers within the article will be joined together using conventional bonding method such as adhesive coating via slot coating, spiral gluing, or spraying on the whole or part of the surface of the layer, or thermo-bonding, or pressure bonding or combinations thereof. Most of the bonding between components is for clarity and readability not represented in the Figure. Typical bonding between the layers of the article should be considered to be present unless specifically excluded. Adhesives may be typically used to improve the adhesion of the different layers, for example between the backsheet and the core wrap. The glues used may be any standard hotmelt glue as known in the art. For example, the backsheet and the core wrap may be glued using a core-to-backsheet gluing pattern as disclosed in WO2012/170341A1 (Hippe), or a full coverage pattern using several spiral glue applicators.

The absorbent article may of course also comprise other typical absorbent article components, which are not represented or further detailed herein, such as a front elastic waist feature, transverse barrier cuff(s), a lotion application, etc. . . .

Packages

Figure 13:
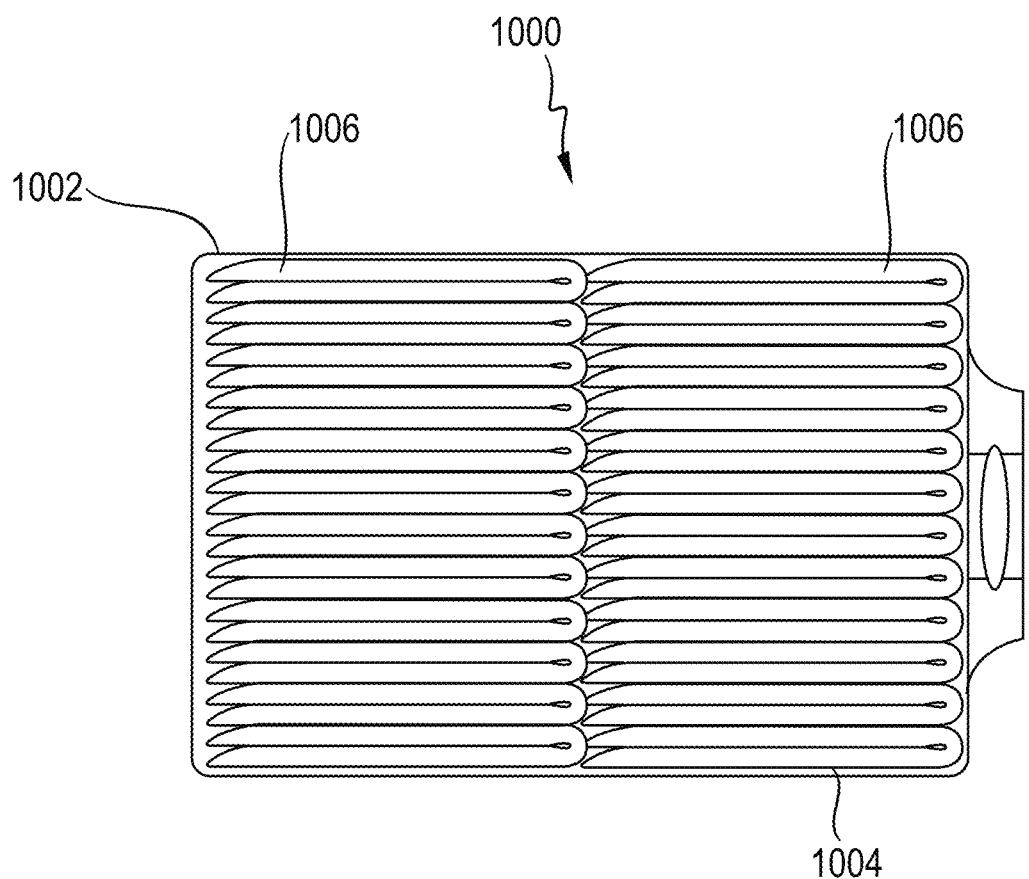
FIG. 13 is a schematic view of a package of absorbent articles.

The articles may be folded and packaged as is known in the art. The package may be for example a plastic bag or a cardboard box. Diapers may typically be bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. FIG. 13 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

The articles of the inventions may be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression may be typically sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of from 42 mm to 200 mm, in particular from 60 mm to 150 mm, or from 70 mm to 140 mm, or from 80 mm to 110 mm, or from 82 mm to 100 mm according to the In-Bag Stack Height Test described below, specifically reciting all 0.1 mm increments within the specified ranges and all ranges formed by combining any upper and lower value.

Examples 1-7 Colored Topsheets

Several colored nonwoven spunbond topsheet materials were prepared from polypropylene pellets compounded with pellets having a mixture of blue and green pigments (Pigment Blue 15 and Pigment Green 7) to obtain a teal shade and optionally adding TiO2 as an opacifying agent. The fibers formed were either conventional round fibers or trilobal fibers. The basis weight of the nonwoven and the amount of opacifying agents (TiO2) were also varied across the examples. Different thermal bonding patterns were used: as in FIG. 5, as in FIG. 9, single type rounded bonds (18 bonds/cm², 2.45 mm×2.08 mm) or with small elongated thermal bonds (49 bonds/cm², 0.882 mm×0.524 mm).

| Example # | Fiber shape | % TiO2 (by weight) | Basis weight (gsm) | Thermal bonds dimensions (μm) | Thermal bonds/cm² | % bonded area |
|---|---|---|---|---|---|---|
| 1 | Trilobal Fiber | 0.3% | 12 | 880 × 520<br>1800 × 2250 | 17 | 22.1 |
| 2 | Trilobal Fiber | 0.3% | 12 | 1500 × 1000<br>1600 × 1400 | 17.6 | 24.2 |
| 3 | Trilobal Fiber | 1.0% | 17 | 880 × 520<br>1800 × 2250 | 17 | 22.1 |
| 4 | Trilobal Fiber | 1.0% | 17 | 1500 × 1000<br>1600 × 1400 | 17.6 | 24.2 |
| 5 | Round Fiber | 0% | 15 | 2450 × 2080 | 6.25 | 24 |
| 6 | Round Fiber | 1% | 15 | 882 × 524 | 49 | 18 |
| 7 | Round Fiber | 1% | 20 | 882 × 524 | 49 | 18 |

The L*a*b* values and the opacity of these materials were measured as indicated herein.

| Example # | L* | a* | b* | Opacity (%) |
|---|---|---|---|---|
| 1 | 89.93 | −8.27 | −1.47 | 30.77 |
| 2 | 90.02 | −7.60 | −1.41 | 30.48 |
| 3 | 89.33 | −11.89 | −1.92 | 45.20 |
| 4 | 89.54 | −10.92 | −1.90 | 42.81 |
| 5 | 90.13 | −7.41 | −1.56 | 25.93 |
| 6 | 90.45 | −7.66 | −1.58 | 31.91 |
| 7 | 90.05 | −9.69 | −1.85 | 39.45 |

Examples 8-9: Diapers with Visual Signal and Colored Topsheet

Two diapers (examples 8 and 9) having the same general construction as shown in FIGS. 1-2 and a visual signal as in FIG. 3 were line made. The acquisition layer was a white 43 gsm carded, resin-bonded nonwoven made out of PET fibers that were bonded by a styrene-butadiene binder. The visual signal was printed using the printed adhesive coating technology described above with a blue adhesive ink on the lower side of the acquisition layer. The topsheet of the first diaper was as in example 2 above, and the topsheet of the second diaper was as in example 4 above. The L*a*b* values on the garment-facing side of the diapers were measured on an area of the topsheet corresponding to colored portion of the visual signal and an area of the topsheet corresponding to the non-colored portion of the visual signal. The ΔE*, ΔL*, Δa*, Δb* values were as follow.

| Example # | Topsheet used | ΔE* | ΔL* | Δa* | Δb* |
|---|---|---|---|---|---|
| 8 | Example 2 | 5.25 | 2.52 | 3.15 | 3.37 |
| 9 | Example 4 | 2.95 | 0.36 | 2.29 | 1.83 |

In both examples, a dual color visual signal was clearly recognizable through the topsheet providing a three dimension appearance to wearer-facing side of the diaper. The topsheet of example 9 was less shiny due to the higher level of TiO2. The bonding pattern in example 9 was also more recognizable due to the higher basis weight of the topsheet.

Test Method: Color Measurement (CIE L*A*b*)

Color measurements are made in accordance with ASTM E1349 using a 0°/45° spectrophotometer suitable for making standard Hunter L*a*b* color measurements (e.g. Spectro-Eye Portable Spectrophotometer, XRite Grand Rapids, Mich., or equivalent). The instrument must be capable of measuring color on a region approximately 2.0 to 3.0 mm in diameter. Analyses are performed in a room controlled at about 23° C.±2 C.° and 50%±2% relative humidity. Samples are conditioned at the same condition for 2 hours before testing. The diameter of the instrument's measurement port should be chosen such that only the region of interest is included within the measurement port.

Calibrate the instrument per the vender instructions using the standard black and white tiles provided by the vendor. Set the spectrophotometer to use the CIE L*a*b* color space, with a D65 standard illumination and 10° observer.

Place the article on a bench top with the top sheet facing upward. Secure the chassis as necessary to the bench to hold the article flat. Visually identify the colored regions that derive their color other than from the color of the topsheet and regions where the color is derived primarily from the topsheet. Carefully center the region to be measured within the instruments aperture and take a reading. Take 10 measures of both colored regions at differing sites across the topsheet and calculate the arithmetic mean for the two different regions for L*a*b* and report to the nearest 0.01 unit. Color differences are calculated in accordance with ASTM D2244. Calculate ΔL*, Δa*, Δb*, ΔE*, and report to the nearest 0.01 unit Test Method: Opacity Opacity by contrast ratio measurements are made using a 0°/45° spectrophotometer suitable for making standard Hunter L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23°

C.±2 C.° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors excise the topsheet specimen from the article for testing. Place the specimen flat against the instrument with the body facing surface toward the spectrophotometer's measurement port and the region of interest within the port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicates specimens.

Opacity is calculated by dividing the Y value measured using the black tile as backing, divided by the Y value measured using the white tile as backing, then multiplying the ratio by 100. Record opacity to the nearest 0.01%. Calculate opacity for the 10 replicates and report the average opacity to the nearest 0.01%.

In-Bag Stack Height Test

The in-bag stack height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure: Absorbent article packages are equilibrated at 23±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Examples/Combinations

A. An absorbent article (20) having a wearer-facing side and a garment-facing side, the article comprising:
  a nonwoven topsheet (24) on the wearer-facing side, wherein the topsheet has a first color which is not white and comprises thermal bonds;
  a backsheet (25) on the garment facing-side;
  an absorbent core (28) between the topsheet and the backsheet;
  optionally an acquisition layer (52); and
  a visual signal disposed on the topsheet or a layer of the article under the topsheet;
  wherein the visual signal comprises a first portion having a first appearance and a second portion having a different second appearance;
  wherein the topsheet has an opacity index of at least 28% as measured by the opacity index test as described herein and, the visual signal is visible on the wearer-facing side of the article.

B. An absorbent article according to paragraph A, wherein the topsheet has an opacity index from 28% to 50%, more preferably from 28% to 43%, more preferably from 29% to 35%.

C. An absorbent article according to paragraphs A or B, wherein the topsheet comprises spunbond fibers, and at least some of the spunbond fibers comprise a colored pigment.

D. An absorbent article according to any of the preceding paragraphs, wherein the topsheet has a basis weight ranging from 10 gsm to 30 gsm.

E. An absorbent article according to any of the preceding paragraphs, wherein the topsheet comprises at least 0.1% TiO2 particles by weight of the topsheet, in particular from 0.2% to 2% TiO2 particles by weight of the topsheet.

F. An absorbent article according to any of the preceding paragraphs, wherein the thermal bonds cover from 15% to 30%, preferably from 20% to 28%, of the surface of the topsheet.

G. An absorbent article according to any of the preceding paragraphs, wherein at least some the thermal bonds have an individual area which ranges from 0.1 mm$^2$ to 10 mm$^2$, in particular from 1 mm$^2$ to 6.0 mm$^2$.

H. An absorbent article according to any of the preceding paragraphs, wherein the first portion of the visual signal is a colored portion and the second portion of the visual signal is a non-colored portion, in particular wherein the colored portion of the visual signal comprises an adhesive comprising an ink.

I. An absorbent article according to the preceding paragraph, wherein the wearer-facing side has a maximum color difference ΔE* between a first area corresponding to the colored portion and a second area corresponding to the non-colored portion of the visual signal, and ΔE* is of at least 2.0, preferably at least 2.5, wherein the color difference is measured according to the CIE L*a*b* space as indicated herein.

J. An absorbent article according to any of the preceding paragraphs, wherein the visual signal is applied on the garment-facing side of the topsheet, or the wearer-facing side of the acquisition layer, or the garment-facing side of the acquisition layer, or the wearer-facing side of the absorbent core.

K. An absorbent article according to any of the preceding paragraphs, wherein the first portion or the second portion of the visual signal comprises a network of intersecting lines (210-21n, 220-22n), in particular wherein the interconnecting lines are oriented diagonally relative to the longitudinal axis (80) of the article, in particular at an angle (a) of ±25°-70° relative to the longitudinal axis, and wherein the areas of the visual signal between the interconnecting lines define repeating units (250-253) orientated in rows parallel to the interconnecting lines.

L. An absorbent article according to the preceding paragraph, wherein at least some of the interconnecting lines have a thickness of at least 1 mm, preferably of at least 2 mm along at least a portion of their length.

M. An absorbent article according to paragraphs K or L, wherein at least some of the rows comprise from 3 to 7 repeating units, in particular from 4 to 6 repeating units.

N. An absorbent article according to any of the preceding paragraphs, wherein the visual signal comprises a pair of curved features (270, 271) that run lengthwise in the longitudinal direction of the absorbent article, wherein each curved feature comprises one more lines that are symmetric to its complement across the longitudinal axis.

O. A package comprising a plurality of the absorbent articles according to any of the preceding paragraphs, wherein the absorbent articles are compressed in the package.

Misc

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer-facing side and a garment-facing side, the article comprising:
    a. a topsheet on the wearer-facing side, the wearer-facing side having a surface area;
    b. a backsheet;
    c. an absorbent core disposed between the topsheet and the backsheet, the absorbent core comprising absorbent material comprising fibers and superabsorbent polymer particles;
    d. an acquisition layer disposed between the absorbent core and the topsheet;
    e. a visual signal viewable from the wearer-facing side of the absorbent article, the visual signal comprising color imparted to the acquisition layer, wherein the visual signal further comprises a plurality of dot-shaped elements disposed on the topsheet and wherein the plurality of dot-shaped elements are thermal bonds and a cumulated area of the plurality of the dot-shaped elements represent 15% to 30% of the surface area of the wearer-facing side;
    f. at least one channel disposed within the absorbent core that is substantially free of absorbent material;
    g. a wetness indicator disposed on the backsheet and viewable from the garment-facing side of the absorbent article;
    h. wherein at least some of the plurality of the dot-shaped elements comprise a surface area of from 1 $mm^2$ to 6 $mm^2$; and
    i. wherein the plurality of dot-shaped elements comprises a first set of bonds having a first dimension and first orientation and a second set of bonds having a second dimension and a second orientation.

2. The absorbent article of claim 1, wherein the plurality of dot-shaped elements are colored.

3. The absorbent article of claim 1, wherein the plurality of dot-shaped elements are non-colored.

4. The absorbent article of claim 1, wherein the topsheet has an opacity index of at least 28% as measured by the Opacity Test herein.

5. The absorbent article of claim 1, wherein the absorbent core comprises a first substrate and a second substrate, and wherein the first substrate is bonded to the second substrate within the at least one channel to form a channel bond.

6. The absorbent article of claim 5, wherein the channel bond comprises point bonds.

7. The absorbent article of claim 5, wherein the channel bond comprises an adhesive bond.

8. The absorbent article of claim 5, wherein the channel bond comprises a heat bond.

9. The absorbent article of claim 5, wherein the channel bond comprises an ultrasonic bond.

10. The absorbent article of claim 5, wherein the channel bond is permanent such that the channel bond does not open when the absorbent article swells.

11. The absorbent article of claim 5, wherein the channel bond at least partially opens when the absorbent article swells.

12. The absorbent article of claim 5, wherein at least one of the first substrate and the second substrate comprises a nonwoven web.

13. The absorbent article of claim 1, wherein the acquisition layer comprises a nonwoven material.

* * * * *